(12) United States Patent
Holm et al.

(10) Patent No.: US 10,500,302 B2
(45) Date of Patent: Dec. 10, 2019

(54) MEDICAL ARTICLES AND METHODS OF MAKING USING MISCIBLE COMPOSITION

(75) Inventors: David R. Holm, Hudson, WI (US); Dong-Wei Zhu, Shoreview, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 573 days.

(21) Appl. No.: 12/942,434

(22) Filed: Nov. 9, 2010

(65) Prior Publication Data

US 2011/0112458 A1 May 12, 2011

Related U.S. Application Data

(60) Provisional application No. 61/259,624, filed on Nov. 9, 2009, provisional application No. 61/301,379, filed on Feb. 4, 2010.

(51) Int. Cl.
*A61L 15/58* (2006.01)

(52) U.S. Cl.
CPC .................................... *A61L 15/58* (2013.01)

(58) Field of Classification Search
CPC .. A61L 15/58; A61L 2400/14; A61F 13/0276; A61F 13/0253; A61F 2013/00876; A61F 13/02; A61F 13/0289; C09J 4/00; C09J 7/0217; C09J 2201/606; C09J 7/38
USPC ................... 602/54, 41, 52; 428/343, 355 R; 424/448
See application file for complete search history.

(56) References Cited

U.S. PATENT DOCUMENTS

| | | | |
|---|---|---|---|
| 2,736,721 A | 2/1956 | Dexter | |
| RE24,906 E | 12/1960 | Ulrich | |
| 4,310,509 A | 1/1982 | Berglund | |
| 4,323,557 A | 4/1982 | Rosso | |
| 4,472,480 A | 9/1984 | Olson | |
| 4,499,896 A | 2/1985 | Heinecke | |
| 4,595,001 A | 6/1986 | Potter | |
| 4,737,410 A * | 4/1988 | Kantner | ............... C09J 133/062 428/343 |
| 4,747,401 A | 5/1988 | Potter | |
| 4,798,201 A | 1/1989 | Rawlings | |
| 4,833,179 A | 5/1989 | Young | |
| 4,871,812 A | 10/1989 | Lucast | |
| 5,120,781 A | 6/1992 | Johnson, Jr. | |
| 5,209,971 A | 5/1993 | Babu | |

(Continued)

FOREIGN PATENT DOCUMENTS

| EP | 1 255 575 | 11/2002 |
|---|---|---|
| WO | WO 2002-066087 | 8/2002 |

(Continued)

OTHER PUBLICATIONS

ASTM Designation: E-96-80, "Standard Test Methods for Water Vapor Transmission of Materials[1]", 1980, pp. 337-346.

(Continued)

*Primary Examiner* — Ophelia A Hawthorne
*Assistant Examiner* — Caitlin A Carreiro
(74) *Attorney, Agent, or Firm* — 3M Innovative Properties Company; Trisha D. Adamson

(57) ABSTRACT

Methods of improving the moisture vapor transmission rate of a pressure sensitive adhesive layer in a medical article with a miscible composition, as well as medical articles including the improved pressure sensitive adhesive layer.

13 Claims, 4 Drawing Sheets

(56) References Cited

U.S. PATENT DOCUMENTS

| | | |
|---|---|---|
| 5,214,119 A | 5/1993 | Leir |
| 5,412,035 A * | 5/1995 | Schmitt ................ C09J 109/06 525/93 |
| 5,531,855 A | 7/1996 | Heinecke |
| 5,622,711 A | 4/1997 | Chen |
| 5,633,010 A | 5/1997 | Chen |
| 5,641,506 A | 6/1997 | Talke |
| 5,731,387 A * | 3/1998 | Zajaczkowski ........ A61L 15/24 525/326.9 |
| 5,738,642 A | 4/1998 | Heinecke |
| 5,849,325 A | 12/1998 | Heinecke |
| 5,908,693 A | 6/1999 | Delgado |
| 6,083,856 A | 7/2000 | Joseph |
| 6,171,985 B1 | 1/2001 | Joseph |
| 6,198,016 B1 | 3/2001 | Lucast |
| 6,262,329 B1 | 7/2001 | Brunsveld |
| 6,264,976 B1 | 7/2001 | Heinecke |
| 6,441,082 B1 | 8/2002 | Weitzel |
| 6,495,229 B1 | 12/2002 | Carte |
| 6,518,343 B1 | 2/2003 | Lucast |
| 6,518,359 B1 | 2/2003 | Clemens |
| 6,548,727 B1 | 4/2003 | Swenson |
| 6,558,790 B1 | 5/2003 | Holguin |
| 6,642,304 B1 | 11/2003 | Hansen |
| 6,838,589 B2 * | 1/2005 | Liedtke ............... A61F 13/0203 602/42 |
| 6,903,151 B2 | 6/2005 | Lucast |
| 7,160,976 B2 | 1/2007 | Lühmann |
| 7,612,248 B2 | 11/2009 | Burton |
| 7,745,509 B2 | 6/2010 | Burton |
| 7,858,838 B2 | 12/2010 | Holm |
| 2003/0054025 A1 | 3/2003 | Cantor |
| 2004/0133143 A1 | 7/2004 | Burton |
| 2006/0159732 A1 | 7/2006 | Cullen |
| 2006/0246296 A1 | 11/2006 | Xia |
| 2008/0107718 A1 | 5/2008 | Baron |
| 2008/0115889 A1 | 5/2008 | Hall |
| 2008/0214712 A1 * | 9/2008 | Passade Boupat ....... C08F 8/44 524/272 |
| 2009/0186221 A1 * | 7/2009 | Yatagai ................ C09J 107/02 428/355 AC |
| 2011/0112457 A1 | 5/2011 | Holm et al. |

FOREIGN PATENT DOCUMENTS

| | | |
|---|---|---|
| WO | WO 2008-074333 | 6/2008 |
| WO | WO 2009-006901 | 1/2009 |
| WO | WO 2009-086840 | 7/2009 |
| WO | WO 2009-088648 | 7/2009 |
| WO | WO 2011-057240 | 5/2011 |

OTHER PUBLICATIONS

ASTM Designation: D3330/D3330M—04 (Reapproved 2010), "Standard Test Methods for Peel Adhesion of Pressure-Sensitive Tape1", 2004, pp. 1-6.

"Glossary of Terms—Pressure Sensitive Tape Council", Pressure Sensitive Tape Council, Naperville, Illinois, USA [on line], [last access date from the internet on Apr. 9, 2012], URL <http://www.pstc.org/i4a/pages/index.cfm?pageid=3336>, 5 pages.

SATAS, Handbook of Pressure Sensitive Adhesive Technology, 172-173 (1989).

Xu, "Microporous Polypropylene Hollow fiber membranes Part II", Journal of Membrane Science, Mar. 2003, vol. 214, No. 1, pp. 71-81.

International Search Report for PCT/US2010/55958, dated Jan. 7, 2011, 5 pages.

International Search Report for PCT/US2010/55778, dated Jan. 7, 2011, 6 pages.

Supplemental EP Search Report for corresponding EP Appln No. 10829218.6, dated Feb. 27, 2014; 4 pgs.

* cited by examiner

MEDICAL ARTICLES AND METHODS OF MAKING USING MISCIBLE COMPOSITION

CROSS-REFERENCE TO RELATED APPLICATIONS

This application claims the benefit of U.S. Provisional Application No. 61/259,624, filed Nov. 9, 2009 and U.S. Provisional Application No. 61/301,379, filed Feb. 4, 2010, both hereby incorporated by reference in their entirety.

BACKGROUND OF THE INVENTION

This disclosure relates to medical articles, and more particularly to wound dressings and medical tapes for use on skin and wounds. Wound dressings and tapes may need to adhere to a variety of skin types and remain effective in the presence of various amounts of moisture, whether a low exuding wound, a high exuding wound, or a patient that is diaphoretic. In all of these circumstances, the wound dressing or tape is desirably able to respond to dynamic levels of moisture present to ensure adequate wear time. Modifications to medical articles to improve permeability to moisture are known and include, for example, selectively or pattern coating an adhesive onto a permeable film surface or creating new adhesives with higher moisture permeability. Examples of selective adhesive coating may include a continuous polymeric thin film having a pressure sensitive adhesive (PSA) that is selectively coated on one surface of the polymeric thin film such that 40 to 75 percent of the film surface does not contain adhesive. Moisture is preferably transmitted through the areas without adhesive.

While the pattern or selective coating may result in medical articles with higher moisture transmission rates, pattern coated adhesive in certain situations can have poor edge adhesion, resulting in edge lift. The methods and equipment used to pattern coat an adhesive can be more expensive and elaborate than the methods and equipment used for coating the adhesive in a continuous film-type manner. In addition, the methods and equipment can be quite specialized for a particular adhesive system and not interchangeable between different adhesive systems.

Methods of creating different adhesive properties are also known, and include adding additives to PSA copolymers. Plasticizers, humectants, inorganic salts, organic salts, or microcolloids may be added to a pressure sensitive adhesive to enhance breathability and make the adhesive suitable for medical articles. Such compounds are fully mixed in and/or dispersed throughout the adhesive prior to construction of a medical article. Thus, the adhesive composition as a whole is made more permeable to moisture by uniform dispersion or mixing of hydrophilic materials. In many cases these uniformly mixed or dispersed additives can significantly change the properties of the adhesive properties throughout the adhesive, especially in the presence of high moisture conditions.

SUMMARY OF THE INVENTION

The present application provides for targeted modification of adhesive systems to improve moisture vapor transmission by providing a moisture vapor transmission rate (MVTR)-modifying composition that is not uniformly dispersed in the bulk of the adhesive layer. In preferred embodiments, the MVTR-modifying material is only minimally dispersed, or not dispersed at all, in the bulk of the adhesive layer. Embodiments of the present invention provide high MVTR medical articles that can be obtained for a wide variety of PSAs instead of or in addition to pattern coating of the adhesive or formulating an inherently high MVTR adhesive system that can also stick adequately to skin under a variety of conditions.

In some embodiments, pressure sensitive adhesives of the present invention advantageously retain consistent adhesive properties prior to contact with fluid in combination with an MVTR-modifying material. Embodiments of the present invention allow for modification of permeability and adhesion in targeted locations in an adhesive layer. As the entire adhesive layer need not be modified, portions of the adhesive layer on the side in contact with a target site, e.g., skin, may retain consistent and desirable adhesion properties regardless of moisture or humidity levels that the adhesive is exposed to during storage or use.

The present invention provides for methods of increasing the MVTR of an adhesive layer in a medical article. In certain embodiments, the method includes: providing a PSA layer including acid-functional groups or basic-functional groups, wherein the PSA includes at least 0.84 mmoles acidic- or basic-functional groups per gram PSA. The method further includes providing an MVTR-modifying composition including an MVTR-modifying material that is basic when the PSA includes an acidic-functional group or is acidic when the PSA includes a basic-functional group, wherein the MVTR-modifying composition is miscible with the PSA; and placing the MVTR-modifying composition in contact with the PSA under conditions effective for at least a portion of the MVTR-modifying composition to penetrate into the PSA layer; wherein contact between the MVTR-modifying material and the PSA causes an acid-base reaction to form a poly-salt and increase the moisture permeability of at least a portion of the PSA layer.

In one embodiment, a method of increasing the MVTR of an adhesive layer in a medical article includes: providing a PSA layer including acid-functional groups or basic-functional groups; providing an MVTR-modifying composition including an MVTR-modifying material that is basic when the PSA includes an acidic-functional group or is acidic when the PSA includes a basic-functional group, wherein the MVTR-modifying composition is miscible with the PSA. The method of further includes placing the MVTR-modifying composition in contact with the PSA under conditions effective for at least a portion of the MVTR-modifying composition to penetrate into the PSA layer to form a non-uniform dispersion; wherein contact between the MVTR-modifying material and the PSA causes an acid-base reaction to form a poly-salt and increase the moisture permeability of at least a portion of the PSA layer.

In certain embodiments, the MVTR-modifying composition further includes a plasticizer, which may be hydrophilic or hydrophobic and which may be reactive or nonreactive with components of the PSA. The plasticizer may assist penetration of the MVTR-modifying material when it is immiscible with the PSA, thereby creating an MVTR-modifying composition that is miscible with the PSA. Non-reactive plasticizers in this embodiment typically include glycerine, propylene glycol, sorbitol, xylitol, maltitol, polydextrose, glyceryl triacetate, urea, hydroxyethylurea, glucose, poly(vinyl alcohol), polyethylene glycols, block copolymers of polyethylene glycol and propylene glycol, and combinations thereof. Reactive plasticizers in these embodiments may include, for example, lactic acid, fatty acids, liquid amines such as triethanolamine, diethanolamine, monoethanolamine, methyldiethanolamine, and combinations thereof. Hydrophilic plasticizers include, for example, compounds containing hydrophilic groups such as hydroxyl groups, amines, carboxylic groups, and esterfied carboxylic groups. Hydrophobic plasticizers may include mineral oils and polypropylene glycol).

In certain embodiments of the methods, the MVTR-modifying composition includes an inorganic acid or an inorganic base. In certain other embodiments, the MVTR-modifying composition includes an organic acid or an organic base.

In certain embodiments, placing the MVTR-modifying composition in contact with the PSA includes pattern coating the MVTR-modifying composition on the PSA layer.

In certain embodiments of the methods, placing the MVTR-modifying composition in contact with the PSA further includes: providing a scaffold; coating the scaffold with the MVTR-modifying composition; and contacting at least a portion of the PSA layer with the coated scaffold. The scaffold can include a variety of substrates suitable to function as a carrier for the MVTR-modifying composition.

In certain embodiments of the methods, PSA layer comprises a comprises a (meth)acrylate polymer, and wherein said polymer is prepared from at least 6 wt-% acidic- or basic-functional monomers, based on the total weight of the PSA.

In certain embodiments of the methods, the PSA includes no greater than 4.2 mmoles acidic- or basic-functional groups per gram PSA.

In certain embodiments, the methods further include providing a backing (i.e., backing layer), and placing the PSA in contact with the backing before or after placing the MVTR-modifying composition in contact with the PSA layer.

A pH-altering layer may be provided as part of certain embodiments of the methods. The methods of these embodiments further include applying the pH-altering layer on the PSA layer after placing the MVTR-modifying composition in contact with the PSA layer.

In one embodiment of the methods providing for a pH-altering layer, the pH-altering layer includes a pH-altering material selected from the group consisting of polyacrylic acid, citric acid, lactic acid or combinations thereof.

A filtration layer may also be provided in certain embodiments of the methods. The method of these embodiments further includes applying the filtration layer on the PSA layer after placing the MVTR-modifying composition in contact with the PSA layer.

In certain embodiments of the methods, the molar ratio of the MVTR-modifying material to the functional groups is 0.1:1 to 100:1 per volume of adhesive under the surface area treated with the MVTR-modifying material.

In certain embodiments of the methods, the PSA layer includes a polymer having acid-functional groups, and the MVTR-modifying composition is basic. In one embodiment of the methods, the MVTR-modifying composition includes an immiscible base selected from a group consisting of sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, hydrates thereof, and combinations thereof. Preferably, the immiscible base is not a multi-valent cation that may cause crosslinking of the PSA polymers to the extent that such crosslinking reduces wet MVTR. In other embodiments of the methods, the MVTR-modifying composition includes a miscible base, such as triethanolamine, methyldiethanolamine, pyridine, benzimidizole, histidine, triethylamine, monoethanolamine, diethanolamine, polyethyleneglycoldiamine, and combinations thereof.

In certain embodiments of the methods, the PSA layer includes a polymer having basic functional groups, and the MVTR-modifying composition is acidic. In one embodiment, the MVTR-modifying composition includes a miscible acid selected from a group consisting of acetic acid, lactic acid, monofunctional fatty acids, or combinations thereof. In other embodiments of the methods the MVTR-modifying composition includes an immiscible acid selected from the group of sulfuric acid, hydrochloric acid, nitric acid, phosphoric acid, formic acid, or combinations thereof.

In one embodiment, the PSA includes rubber based adhesives (e.g., tackified natural rubbers, synthetic rubbers, and styrene-butadiene block copolymers), (meth)acrylics (i.e., (meth)acrylates), poly(alpha-olefins), polyurethanes, silicones, and combinations thereof. In certain embodiments, the PSA includes an amine adhesive (e.g., that includes a polymer with basic amine groups in the backbone, pendant therefrom, or both). In certain embodiments, the PSA includes a polymer having carboxylic acid groups. In certain embodiments, the acid groups, or part of the acid groups, in the PSA can be incorporated by mixing tackifiers or other additives with the above mentioned polymers.

In certain embodiments, the medical article created by the methods has a wet MVTR of at least 1200 $g/m^2/24$ hours. In certain embodiments, the MVTR-modifying composition improves (i.e., increases) the dry and/or the wet MVTR of the medical article by at least 20% relative to the same article without the MVTR-modifying composition.

The present invention also provides a method of applying a plasticizer to a PSA layer in a medical article. The method includes: providing a PSA layer including acid-functional groups or a basic-functional groups; providing a plasticizer; providing a scaffold; coating the scaffold with the plasticizer; and contacting at least a portion of the PSA layer with the coated scaffold.

The present invention further provides for a medical article prepared by methods of embodiments described above. In one embodiment, the medical article is a wound dressing.

The present invention also provides for medical articles including: a PSA layer including a PSA including acid-functional groups or basic-functional groups; an MVTR-modifying composition that is basic when the PSA includes an acidic-functional group or is acidic when the PSA includes a basic-functional group; and ionic groups non-uniformly distributed throughout the PSA layer, wherein the ionic groups are formed from the reaction of the PSA functional groups and the MVTR-modifying composition. In certain embodiments, the medical article further includes a plasticizer. In certain embodiments, the PSA includes at least 0.84 mmoles acidic- or basic-functional groups per gram PSA.

In certain embodiments a medical article of the present invention includes: a PSA layer including acid-functional groups or basic-functional groups, wherein the PSA includes at least 0.84 mmoles acidic- or basic-functional groups per gram PSA; a hydrophilic plasticizer; and an MVTR-modifying material that is basic when the PSA includes acidic-functional group or is acidic when the PSA includes basic-functional groups; wherein the MVTR-modifying material is immiscible with the PSA, and reacts with the functional groups of the PSA upon contact to form a poly-salt in the presence of fluid.

In one embodiment of the present invention, the medical article is a wound dressing. The wound dressing may include: a backing (i.e., backing layer) having a first major surface and a second major surface; a PSA layer disposed on at least a portion of the first major surface of the backing; wherein the PSA includes acid-functional groups or basic-functional groups, wherein the PSA includes at least 0.84 mmoles acidic- or basic-functional groups per gram PSA; a hydrophilic plasticizer; and an MVTR-modifying layer proximate the PSA layer; wherein the MVTR-modifying layer includes an MVTR-modifying material that is basic when the PSA includes acidic-functional groups, or is acidic when the PSA comprises basic-functional groups; wherein the MVTR-modifying material is immiscible with the PSA, and reacts with the functional groups to form a poly-salt upon contact in the presence of fluid. An MVTR-modifying composition may include an immiscible component and a miscible component (i.e., a plasticizer) and still be a miscible MVTR-modifying composition.

In one embodiment a wound dressing of the present invention includes: a backing having a first major surface and a second major surface; a PSA layer disposed on at least a portion of the first major surface of the backing; wherein the PSA layer includes acid-functional groups; a support layer releasably adhered to the second major surface of the backing; a hydrophilic plasticizer; and an MVTR-modifying layer including an MVTR-modifying material in contact with the PSA layer, wherein the PSA layer does not include MVTR-modifying material uniformly dispersed throughout; wherein the MVTR-modifying material is basic, is immiscible with the PSA, and reacts with the functional groups to form a poly-salt upon contact in the presence of fluid.

The ability to modify MVTR, instead of (or in addition to) pattern coating an adhesive on a permeable film or mixing hydrophilic additives to the adhesive in bulk, makes the present invention particularly well suited for medical articles such as medical tapes, bandages, feminine hygiene pads, diapers, surgical drapes, and various wound dressings. A practitioner or manufacturer may effectively control the level of moisture permeability for a given portion of an adhesive layer, allowing for narrow tailoring to the nature and requirements of the patient's malady. Instead of a compromise between adhesion and permeability, the present invention allows for optimization of both of these characteristics.

Herein, "fluid" means water, water vapor, serum, wound exudate, sweat, and other liquid or vapor compositions.

Herein, "layer" means a single stratum that may be continuous or discontinuous over a surface.

Herein, "absorbent" means that the material is preferably capable of absorbing fluids, particularly body fluids.

Herein, "poly-salt" means a polymer having at least one ionic group.

Herein, "MVTR-modifying composition" means a composition that includes MVTR-modifying material, plasticizer, and combinations thereof.

Herein, "miscible" or "compatible" means that a material is capable of penetrating into the core (i.e., center) of a 0.25 centimeter (cm) cross-section of an adhesive layer. To examine compatibility, a small portion of an adhesive polymer may be cut into a 0.25 cm thick×2.5 cm wide×10 cm long strip. The polymer is then placed in contact with the MVTR-modifying composition for 24 hours at 25 degrees Celsius and 20% to 50% relative humidity. A cross-section of the adhesive strip is then analyzed for presence of MVTR-modifying composition at the center of the section. A compatible or miscible material is capable of penetrating into the core (i.e., center) of a 0.25 centimeter (cm) cross-section of an adhesive layer.

Herein, a "miscible MVTR-modifying composition" is a composition that includes at least one component that is miscible with the PSA. For example, if the miscible MVTR-modifying composition includes an immiscible acid or base, the composition also includes a miscible component (e.g., a hydrophilic plasticizer).

Herein, "immiscible" or "incompatible" means that a material is not capable of penetrating into the core of a 0.25 centimeter (cm) cross-section of an adhesive layer.

Herein, "medical article" means wound dressings, surgical drapes, tapes, bandages, diapers, feminine hygiene products, and combinations thereof. Preferred medical articles include tapes, wound dressings, and bandages.

Herein, "hydrophilic" means a material that has an HLB (hydrophile/lipophile/balance) value of at least 5, preferably at least 8, and more preferably at least 13.

Herein, "PSA comprising an acidic-functional group," "polymer comprising an acidic-functional group," "PSA comprising acidic functional groups" or "polymer comprising acidic-functional groups" means that the PSA, or polymer included therein, has an excess of acidic groups (e.g., carboxylic acid groups) if there are both acidic and basic groups present such that the PSA, or polymer included therein, is acidic.

Herein, "PSA comprising a basic-functional group," "polymer comprising a basic-functional group," "PSA comprising basic functional groups" or "polymer comprising basic-functional groups" means that the PSA, or polymer included therein, has an excess of basic groups if there are both acidic and basic groups present such that the PSA, or polymer included therein, is basic.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, an adhesive polymer that comprises "an" acid functional group can be interpreted to mean that the adhesive polymer includes "one or more" acid functional groups. Similarly, a medical article comprising "a" filtration layer can be interpreted to mean that the composition includes "one or more" filtration layers.

Also herein, the recitations of numerical ranges by endpoints include all numbers subsumed within that range (e.g., 1 to 5 includes 1, 1.5, 2, 2.75, 3, 3.80, 4, 5, etc.).

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

The invention will be further described with reference to the drawings, wherein corresponding reference characters indicate corresponding parts throughout the several views, and wherein.

Figure 1:
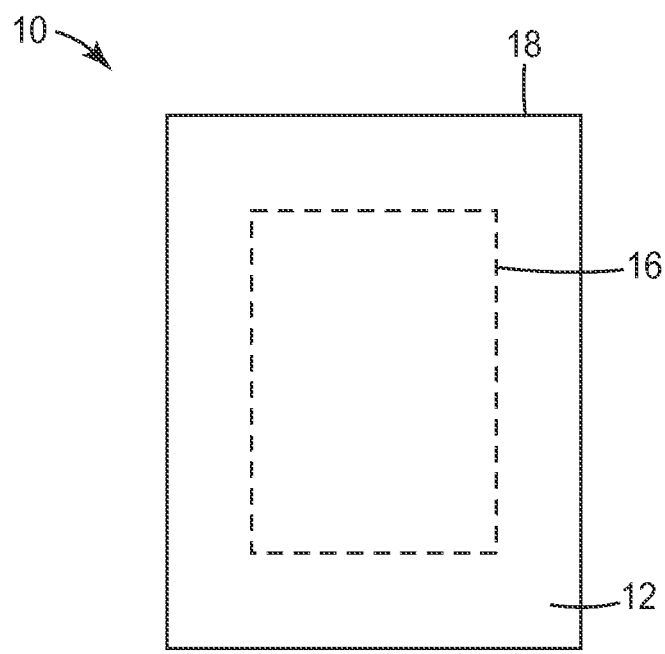
FIG. 1 is a top view of a wound dressing according to one embodiment of the present invention.

The MVTR-modifying composition may be depicted in the Figures as confined to discrete portions of the medical article. This is intended to depict the MVTR-modifying composition at a moment in time before it diffuses or disperses into the PSA layer. Thus, depictions are intended to show the possible orientations of MVTR-modifying composition when initially placed in contact with the PSA layer. Layers in the depicted embodiments are for illustrative purposes only and are not intended to define the relative thickness or position of any component.

DETAILED DESCRIPTION OF ILLUSTRATIVE EMBODIMENTS

The present invention is directed to a medical article having a PSA layer and methods of making medical articles more permeable to moisture. Through the use of different MVTR-modifying compositions and different concentrations of MVTR-modifying compositions, the PSA layer may be modified to meet desired adhesion properties and moisture vapor transmission properties. For example, modified wound dressings of the present invention may have a relatively low dry MVTR and a relatively high wet MVTR in locations that vary within the dressing and different adhesion properties that vary within the dressing. These MVTR properties are important to allow the wound under the dressing to heal in moist conditions without causing the skin surrounding the wound to become macerated, and to facilitate optimum wear time and ease of removal.

In some embodiments of the invention, an MVTR-modifying layer includes an MVTR-modifying composition that interacts with the acid or base functional groups in a PSA layer. For example, if PSA includes functional groups that are basic, the MVTR-modifying composition will be acidic. Similarly, if the PSA includes functional groups that are acidic, the MVTR-modifying composition will be basic. The MVTR-modifying composition may be placed on or near a surface of the PSA layer.

Herein, dry MVTR (or upright MVTR) of the PSA layer, or the medical article, is measured by ASTM E-96-80 (American Society of Testing Materials) at 40° C. and 20% relative humidity using an upright cup method. Wet MVTR (or inverted MVTR) is measured by the same method except that the sample jars are inverted so the water is in direct contact with the test sample.

Factors influencing the MVTR include, but are not limited to, the thickness of the PSA layer, concentration of acid/base functionality within the PSA layer, the amount of MVTR-modifying composition, the composition and structure of the backing film, the coating structure (i.e., continuous, fibrous, film, or pattern) of the adhesive, and the overall construction of a medical article (e.g., number and arrangement of various layers, films, etc.). When compared to the dry MVTR of an untreated medical article of identical composition and construction with a continuous layer of adhesive, the dry MVTR of the medical article that has been treated with MVTR-modifying composition according to the present invention is preferably greater than the untreated medical article by a factor of at least 1.2 (at least 20%) more, preferably at least 3, even more preferably at least 5, and even more preferably at least 10.

When compared to the wet MVTR of an untreated medical article of identical composition and construction, the wet MVTR of the medical article that has been treated with MVTR-modifying composition according to the present invention is preferably greater than the untreated medical article by a factor of at least 1.2 (at least 20%) more, preferably at least 3, even more preferably at least 5, and even more preferably at least 10. The medical article that has been treated preferably has a wet MVTR of at least 1200 g/m$^2$/24 hours, more preferably at least 3000 g/m$^2$/24 hours, even more preferably at least 7500 g/m$^2$/24 hours, and even more preferably at least 15000 g/m$^2$/24 hours. Different regions of the medical article may include different MVTR values.

In embodiments of the invention wherein an MVTR-modifying composition includes an MVTR-modifying material, the PSA layer is modified at least partially due to an acid-base interaction. Such an acid-base interaction is a Lewis acid-base type interaction. Lewis acid-base interactions require that one chemical component be an electron acceptor (acid) and the other an electron donor (base). The electron donor provides an unshared pair of electrons and the electron acceptor furnishes an orbital system that can accommodate the additional unshared pair of electrons. The following general equation describes the Lewis acid-base interaction:

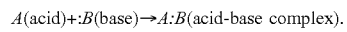

$$A(\text{acid})+:B(\text{base}) \rightarrow A:B(\text{acid-base complex}).$$

The MVTR-modifying composition of the present invention is miscible in or compatible with the PSA polymer (as herein defined, a miscible MVTR-modifying composition includes at least one component that is miscible with the PSA) when the article is not in contact with fluid, such as water or moisture. Accordingly the MVTR-modifying composition will migrate within or substantially penetrate the adhesive in the absence of fluid. When the MVTR-modifying composition reacts in certain embodiments with the adhesive layer, a Lewis acid-base reaction occurs and portions of the adhesive are neutralized. This neutralization and creation of ionic bonds increases the polarity of discrete portions of the adhesive layer, which results in increased MVTR. This penetration does not result in a uniform dispersion of MVTR-modifying composition throughout the entire adhesive layer.

In some embodiments, the modification of the PSA by the MVTR-modifying composition is independent of the particular functionality on the respective PSA and MVTR-modifying material within the MVTR-modifying composition. That is, either the PSA or the MVTR-modifying material can contain the acid or the base functionality. For example, an acid functionalized polymer in the adhesive layer can be paired with a basic MVTR-modifying composition (i.e., an MVTR-modifying composition that includes a basic MVTR-modifying material). Alternatively, a base functionalized group in the adhesive layer can be paired with an acidic MVTR-modifying composition (i.e., an MVTR-composition that includes an acidic MVTR-modifying material).

The MVTR-modifying composition may include a base or an acid, a plasticizer, and combinations thereof. In embodiments wherein the MVTR-modifying composition includes an immiscible MVTR-modifying material, the MVTR-composition also includes a plasticizer. In embodiments wherein the MVTR-modifying composition includes a miscible MVTR-modifying material, the MVTR-modifying composition may or may not include a plasticizer.

In one embodiment of the invention, the MVTR-modifying composition includes an immiscible MVTR-modifying material that is an inorganic base. Suitable examples of inorganic bases are sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, the hydrates of these inorganic bases, and combinations thereof. In preferred embodiments, the MVTR-modifying composition includes sodium carbonate, sodium bicarbonate, potassium carbonate, or potassium bicarbonate, hydrates thereof, and combinations thereof. Preferably, the immiscible base is not a multi-valent cation that may cause crosslinking of the PSA polymers to the extent that such crosslinking reduces wet MVTR. In certain preferred embodiments, the MVTR-modifying material has a water solubility of greater than 50 mg/L at 25° C.

In another embodiment of the invention, the MVTR-modifying composition includes an immiscible MVTR-modifying material that is an organic base. Suitable organic bases include, but are not limited to poly(ethyleneimine), poly(ethyloxazoline), other polymers containing amino functional groups such as poly(N,N-dimethylaminoethyl acrylate), and combinations thereof.

In some embodiments, the MVTR-modifying composition includes an immiscible MVTR-modifying material that is an inorganic acid. Suitable examples of inorganic acids include, but are not limited to, sulfuric acid, hydrochloric acid, nitric acid, phosphoric acid, and mixtures thereof. In another embodiment, the MVTR-modifying material is an immiscible organic acid, such as formic acid, for example. Preferably, the immiscible organic acid is monofunctional.

In some embodiments, the MVTR-modifying composition includes a miscible MVTR-modifying material that is an organic base. Suitable examples of organic bases include, but are not limited to, triethanolamine, methyldiethanolamine, pyridine, benzimidizole, histidine, triethylamine, monoethanolamine, diethanolamine, other amine containing compounds, and combinations thereof.

In some embodiments, the MVTR-modifying composition includes a miscible MVTR-modifying material that is an organic acid. Suitable examples of miscible organic acids include, but are not limited to, acetic acid, lactic acid, other monofunctional fatty acids, monofunctional carboxylic acids, and combinations thereof.

In certain embodiments of the present invention, particularly those including an immiscible MVTR-modifying material, the MVTR-modifying composition includes a plasticizer. Plasticizer may be hydrophilic or hydrophobic and may be reactive or nonreactive with components of the PSA. The plasticizer may assist penetration of the immiscible MVTR-modifying material, thereby creating an MVTR-modifying composition that is miscible with the PSA. Nonreactive plasticizers in this embodiment typically include glycerine, propylene glycol, sorbitol, xylitol, maltitol, polydextrose, glyceryl triacetate, urea, hydroxyethylurea, glucose, poly(vinyl alcohol), polyethylene glycols, block copolymers of polyethylene glycol and propylene glycol available from BASF, Germany under the trade name PLURONIC, and combinations thereof. Reactive plasticizers in these embodiments may include, for example, lactic acid, fatty acids, liquid amines such as triethanolamine, diethanolamine, monoethanolamine, methyldiethanolamine, and combinations thereof. Hydrophilic plasticizers include, for example, compounds containing hydrophilic groups such as hydroxyl groups, amines, carboxylic groups, and esterfied carboxylic groups. Hydrophobic plasticizers may include mineral oils, poly(propylene glycol) and other hydrophobic plasticizers known to those having skill in the art.

For a given treatment area (i.e., volume of PSA confined within the initial surface area treated), the level of plasticizer needed to desirably increase the MVTR through the adhesive is based on the relative mass of plasticizer to adhesive utilized. Preferably, the mass ratio of plasticizer to adhesive for a given treatment area (i.e., the volume under the initial surface area treated) should range from about 0.05:1 to 20:1. More preferably, this ratio is 0.1:1 to 10:1, and even more preferably 0.2:1 to 5:1.

It is further contemplated that the plasticizer could be used to deliver moisture to the wound or other target site. In these embodiments, MVTR-modifying composition may include glycerine or hydroxyethylurea.

Polymers suitable for PSAs in the present invention are those containing acidic or basic functionalities which on neutralization yield ionic functionalities. Additionally or alternatively, the acid groups, or part of the acid groups, in the PSA can be incorporated by mixing acid-functional tackifiers or other acid-functional additives with the polymers of the PSA. Such groups, whether as part of the PSA polymer or other additives, may be the same or different. Similarly, the basic groups, or part of the basic groups, in the PSA can be incorporated by mixing tackifiers or other additives with the polymers of the PSA. Such groups, whether as part of the PSA polymer or other additives, may be the same or different.

As used in the present invention, an "acidic-functional polymer" is a polymer that includes acidic-functional groups, which can be, for example, derived from at least one acidic monomer and at least one non-acidic copolymerizable monomer (i.e., a monomer that can not be titrated with a base). Alternatively, polymers can be chemically modified to include acidic functional groups. The acidic polymer may optionally include other copolymerizable monomers, such as vinyl monomers and basic monomers, as long as the resultant polymer can still be titrated with a base. Thus, usually more acidic monomers are utilized to prepare the acidic polymers than basic monomers. The acid-functional groups in any one polymer may be the same or different.

A "basic-functional polymer" is a polymer that includes basic-functional groups, which can be, for example, derived from at least one basic monomer and at least one nonbasic copolymerizable monomer (i.e., a monomer that cannot be titrated with an acid). Alternatively, polymers can be chemically modified to include basic functional groups. Other monomers can be copolymerized with the basic monomers (e.g., acidic monomers, vinyl monomers, and (meth)acrylate monomers), as long as the basic copolymer retains its basicity (i.e., it can still be titrated with an acid). Also, a basic-functional polymer can be an amine-containing polymer, wherein the amine groups are in the backbone, pendant therefrom, or both. The basic-functional groups in any one polymer may be the same or different.

For a given treatment area, defined as the volume of PSA confined within the initial surface area treated, the level of MVTR-modifying composition needed to increase the MVTR through the adhesive is based on the relative molar amounts of base/acid functional groups of the MVTR-modifying material within the MVTR-modifying composition to the acid/base functional groups of the adhesive that are available for neutralization for a given treatment area. Preferably, the molar ratio of MVTR-modifying material in the MVTR-modifying composition to the total acid/base functional groups in the adhesive per given volume treated (i.e., the volume under the surface area treated) should range from 0.1:1 to 100:1. More preferably, this ratio is 0.2:1 to 50:1, and even more preferably 0.4:1 to 25:1.

In an embodiment wherein the MVTR-modifying composition includes immiscible MVTR-modifying material and a plasticizer, the molar ratio of plasticizer to the immiscible MVTR-modifying material used should range from 0.1:1 to 20:1, more preferably from 0.2:1 to 10:1, and most preferably, 0.4:1 to 5:1.

In some embodiments, the adhesive contains greater than 0.42 mmoles of acidic- or basic-functional groups per gram of PSA that can be neutralized by the MVTR-modifying material. More preferably, the adhesive contains at least 0.69 mmoles of these functional groups per gram of PSA. Even more preferably, the adhesive contains 0.84 mmoles of these functional groups. Even more preferably, the adhesive contains at least 1.3 mmoles of these functional groups. Even more preferably, the adhesive contains at least 1.80 mmoles of these functional groups. Even more preferably, the adhesive contains at least 2.08 mmoles of these functional groups. In most embodiments, the adhesive contains between 1.3 mmoles and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In some embodiments of the present invention, the MVTR-modifying composition is initially in direct contact with the PSA layer. The MVTR-modifying composition can be directly disposed on the surface or may alternatively be incorporated into a scaffold, in both circumstances creating an initial MVTR-modifying layer in contact with a surface of the PSA. The MVTR-modifying layer may extend continuously across a portion to the PSA layer surface or may be disposed in discrete locations. In additional embodiments of the present invention, a filtration layer can be disposed between the target site and MVTR-modifying layer or alternatively between the PSA layer and the MVTR-modifying layer. In other embodiments of the invention, a pH-altering layer is disposed between the target site and the MVTR-modifying layer to modify pH. In some embodiments, the medical article of the present invention may include a backing layer (i.e., backing) In another embodiment, the MVTR-modifying layer can be disposed between a first and second PSA layer.

The methods described herein involve use of an aqueous (i.e., water) solution to dispose the MVTR-modifying composition on a substrate (e.g., the PSA layer, the scaffold, etc.). It is also envisioned that other solvents known to those having skill in the art can be utilized. As can also be appreciated by those having skill in the art, methods of making can utilize a neat MVTR-modifying composition (i.e., without a solvent).

Figure 2:
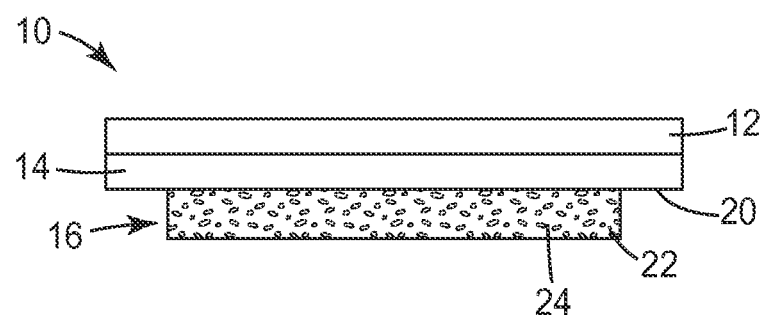
FIG. 2 is a side view of the wound dressing of FIG. 1.

Starting with reference to FIGS. 1 and 2, a wound dressing according to one embodiment of the disclosure is depicted. FIG. 1 is a top view of the wound dressing, and FIG. 2 is a side view of the wound dressing of FIG. 1. Wound dressing 10 includes a backing layer 12, a PSA layer 14 on one surface of the backing layer 12, and an MVTR-modifying layer 16 attached to a portion of the PSA layer 14. The MVTR-modifying layer 16 does not fully extend to the periphery 18 of the PSA layer 14, so that portions of the exposed surface 20 of the PSA layer 14 are not in contact with the MVTR-modifying layer 16. It is also contemplated that in some embodiments the MVTR-modifying layer extends to the periphery of the PSA layer, in that the MVTR-modifying layer and the PSA layer are coextensive.

According to the embodiment depicted in FIGS. 1 and 2, the MVTR-modifying layer 16 is comprised of a scaffold 22 and an MVTR-modifying composition 24 incorporated into or deposited on the surface of said scaffold 22. Exemplary materials useful for the scaffold are described in further detail below. As depicted in FIG. 2, the MVTR-modifying layer 16 is a layer on a portion of the PSA layer 14. The MVTR-modifying layer 16 may be centrally located on the surface of the PSA layer 14, or it may be offset in any direction. Location of the MVTR-modifying layer 16 relative to the center of the dressing may be governed by the nature and location of the target site and the intended application of the modified adhesive layer 14. A given treatment area can be defined by the portions of the MVTR-modifying layer 16 in contact with or attached to the surface of the PSA layer 14. In some embodiments, this limited contact area and relative molar concentrations of reactive groups could serve to prevent the entire PSA layer 14 from being modified by the MVTR-modifying composition 24. Targeted modification in the treatment area with certain embodiments of the MVTR-modifying composition could allow for portions of the PSA layer 14 to retain desirable adhesion to skin when in contact with fluid.

MVTR-modifying composition may be impregnated in or deposited on the scaffold by any suitable method for adding the desired material to a substrate. FIG. 2 depicts the former embodiment, wherein the scaffold 22 is impregnated with MVTR-modifying composition 24. In one embodiment, the scaffold is dip coated in an aqueous solution containing a concentration of the MVTR-modifying composition. The scaffold is saturated and then drawn out of the aqueous solution. The scaffold is then dried. In some embodiments, the MVTR-modifying composition in the aqueous solution includes a concentration of an organic acid or base. In other embodiments, the MVTR-modifying composition in the aqueous solution includes a concentration of an organic acid or base and a concentration of an inorganic acid or base. In further embodiments, aqueous solution of the MVTR-modifying composition may include an organic acid or base, an inorganic acid or base, a plasticizer, and combinations thereof. It is further contemplated that the scaffold retains some moisture before contact with the PSA layer. In some embodiments, the aqueous solution of MVTR-modifying composition includes a concentration of a plasticizer and an acid or base.

Alternatively, the MVTR-modifying composition 24 may be initially deposited onto a surface of the scaffold 22. In one such embodiment, the MVTR-modifying composition is pattern coated onto the surface of the scaffold. Droplets of an aqueous solution comprising a concentration of MVTR-modifying composition may be created and placed on the surface of the scaffold. The aqueous solution may further include a concentration of C1-C4 alcohol that is readily removed during drying.

The droplets of MVTR-modifying composition may be placed on a surface of the scaffold or the adhesive in any number of patterns, including but not limited to, discrete wells, parallel rows or columns, and intersecting mesh networks. These same methods could be used to directly apply the MVTR-modifying composition to the PSA layer.

In further embodiments of the invention, incorporation of the MVTR-modifying composition may be achieved by coating of surfaces or impregnation of substrates with solutions, pure materials, or particle loading of webs. These coating or impregnation methods include flood coating, spray coating, pattern coating using a gravure roll, knife coating, slot die coating, inkjet printing, powder coating, or particle loading of webs. It is clear to one of skill in the art upon reading the present application that the MVTR-modifying composition is not mixed within the adhesive before it is attached to a substrate, but is instead applied to a surface after such attachment occurs.

Once scaffold 22 has been impregnated or coated with MVTR-modifying composition 24 to form the MVTR-modifying layer 16, the MVTR-modifying layer 16 may be attached to the PSA layer 14 by methods known to those skilled in the arts of converting, lamination, coating, and/or needle tacking.

Alternatively or additionally, the MVTR-modifying composition can be directly applied the PSA layer and/or the backing layer. For example, the PSA can be directly laminated to or coated on a backing layer that has been coated with MVTR-modifying composition. For an island type dressing, individual pads containing the MVTR-modifying composition can be cut from a web and placed on an adhesive coated backing using rotary converting, and other converting methods known to those having skill in the art. For a multi-layer product, there are a variety of methods of attaching the MVTR-modifying layer to the adhesive layer such as lamination and rotary converting, and other converting methods known to those having skill in the art.

Figure 3A:
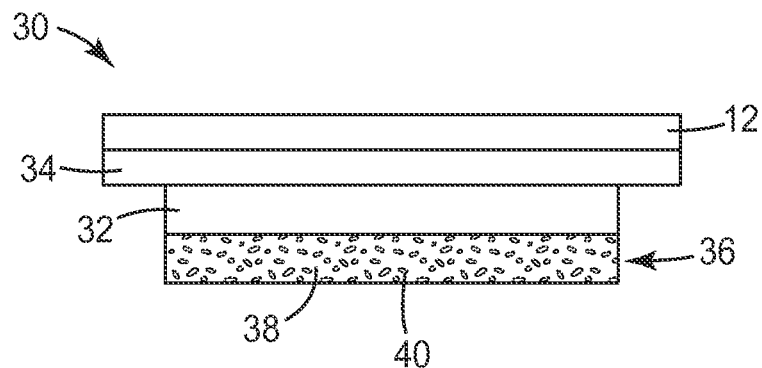
FIG. 3a is a side view of a wound dressing according to a further embodiment of the present invention.
Figure 3B:
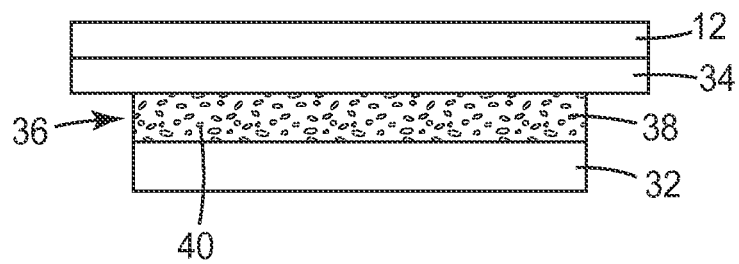
FIG. 3b is a side view of the wound dressing according to a further embodiment of the present invention.

FIGS. 3a and 3b depict additional embodiments of the disclosure. A wound dressing 30 may further include a filtration layer 32 in addition to an adhesive layer 34 and an MVTR-modifying layer 36. Like MVTR-modifying layer 16 of the previous embodiment, the MVTR-modifying layer 36 comprises a scaffold 38 and an MVTR-modifying composition 40. The filtration layer 32 does not initially incorporate an MVTR-modifying composition, although the MVTR-modifying composition may migrate into the filtration layer 32 once constructed.

In the embodiment depicted in FIG. 3a, the filtration layer 32 is disposed between the adhesive layer 34 and the MVTR-modifying layer 36. Accordingly, the MVTR-modifying layer 36 and the MVTR-modifying composition are not in contact with the adhesive layer 34 when the medical article is initially constructed. As the MVTR-modifying composition diffuses through a surface of the filtration layer it may migrate through the filtration layer 32 to the adhesive layer 34.

FIG. 3b depicts an alternative embodiment of the invention, wherein one or more filtration layers 32 are disposed on the target site-facing side (e.g., wound-facing side) of the MVTR-modifying layer 36. As before, the MVTR-modifying composition 40 will disperse once it is placed in contact with the PSA layer. The filtration layer 32 in this configuration may be used to selectively filter molecules that might be present in the fluid generated by the wound or other target site. The filtration layer 32 serves to reduce premature neutralization or deactivation of the MVTR-modifying composition 40. The aforementioned filtering may occur physically, with specifically designed porosity, for example. It is also contemplated that a second filtration layer may be positioned between the adhesive layer 34 and the MVTR-modifying layer 36, as is shown in FIG. 3a. The filtration layer 32 could alternatively or additionally be a pH-altering layer.

Figure 4:
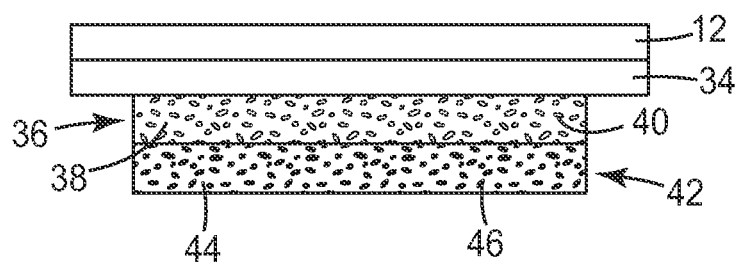
FIG. 4 is a side view of a wound dressing in a further embodiment of the present invention.

Turning to FIG. 4, another embodiment includes a pH-altering layer 42 disposed between the MVTR-modifying layer 36 and the target site. The pH-altering layer 42 includes a pH-altering material 46. In some embodiments, the pH-altering material 46 has a different pKa or pKb than the pKa or pKb of the MVTR-modifying composition 40. The pH-altering material may include citric acid, polyacrylic acid, other pH-altering materials known to those having skill in the art, and combinations thereof. For example, the pH-altering layer 42 may include citric acid, and the MVTR-modifying composition may include an inorganic base, such as sodium carbonate. Other combinations are contemplated and possible. Inclusion of the pH-altering layer 42 with pH-altering material 46 to the medical article may provide buffering capabilities in order to minimize overall pH change of the fluid as it passes through the layers. Although not wishing to be bound by theory, the pH-altering layer 42 in this embodiment may also serve to prevent the MVTR-modifying composition 40 from adversely modifying the pH of a target site. Although not shown in FIG. 4, the pH-altering layer 42 may extend beyond the periphery of the MVTR-modifying layer and be attached to the adhesive layer 34.

The filtration layer 32 and/or pH-altering layer 42 may include the same or similar material as scaffold 38. The filtration layer 32 and/or pH-altering layer 42 may also include a different material, though preferably one that is capable of absorbing moisture. The pH-altering material 46 may be incorporated into a second scaffold 44 or deposited on the surface thereof by using various methods as described above.

Figure 5:
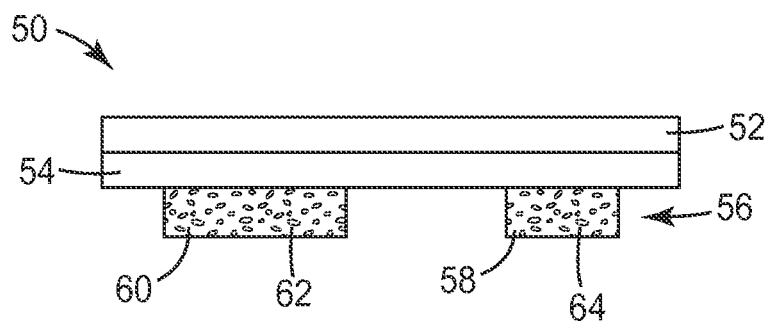
FIG. 5 is a side view of a wound dressing in a further embodiment of the present invention.

FIG. 5 depicts a wound dressing according to one embodiment of the invention. Unlike the other embodiments heretofore depicted, wound dressing 50 includes a discontinuous MVTR-modifying layer 56 that includes scaffolds. As depicted in FIG. 5, MVTR-modifying layer 56 is comprised of two or more scaffolds (58, 60) on separate portions of the adhesive layer 54, which is disposed on a backing layer 52. Both scaffolds (58, 60) may incorporate MVTR-modifying composition (62, 64). The MVTR-modifying composition 64 incorporated in the first scaffold 58 may be the same as the MVTR-modifying composition 62 incorporated into the second scaffold 60, so that the MVTR of the adhesive layer 54 exposed to the MVTR-modifying composition (62, 64) is essentially the same. It is also contemplated that the two MVTR-modifying compositions (62, 64) may be different or present at different concentrations, such that portions of the adhesive layer 54 may have varying MVTR at a certain point in time.

Figure 6:
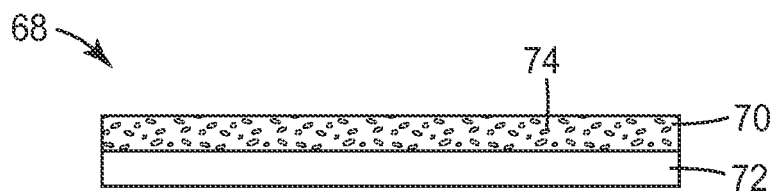
FIG. 6 is a side view of a medical tape according to an embodiment of the present invention.

The concepts of the present invention may also be utilized to create surgical tapes or similar articles. FIG. 6 depicts such an embodiment. Surgical tape 68 includes a backing layer 70 and a pressure sensitive adhesive layer 72 on one surface of the backing layer 70. MVTR-modifying composition 74 is incorporated into the backing layer 70 by methods as described above.

Figure 7:
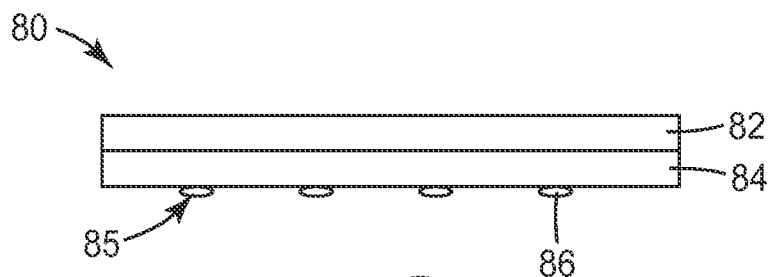
FIG. 7 is a side view of a medical article in a further embodiment of the present invention.

In an alternative embodiment, MVTR-modifying composition may be deposited, coated, or placed directly on a surface of the PSA layer. As depicted in FIG. 7, medical article 80 comprises a PSA layer 84 disposed on backing layer 82. The MVTR-modifying layer 85 initially includes discrete portions of MVTR-modifying composition 86, but does not include a scaffold on the target site-facing surface. Alternatively or additionally, the PSA layer 84 may also include sections of MVTR-modifying composition 86 on discrete portions of the surface between the PSA layer 84 and the backing layer 82. It is contemplated, though not depicted, that the embodiment further include filtration layers affixed to the target site-facing surface of the adhesive layer 84.

MVTR-modifying composition 86 may be placed in contact with the adhesive layer 84 by various methods as described above, including, but not limited to, pattern, spray, and powder coating. In operation, this method of MVTR modification allows for selective and localized modification of moisture permeability and adhesion without the inclusion of a scaffold. In preferred embodiments, the MVTR-modifying composition placed directly on the surface of the PSA layer includes a plasticizer and an immiscible MVTR-modifying material.

Figure 8:
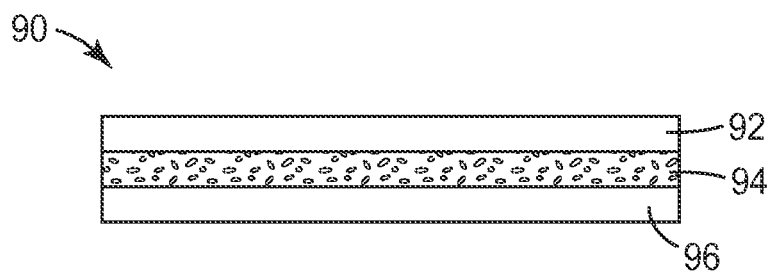
FIG. 8 is a side view of a medical article in a further embodiment of the present invention.

FIG. 8 depicts another embodiment of the disclosure, wherein medical article 90 includes an MVTR-modifying layer 94 is disposed between a backing layer 92 and a PSA layer 96. MVTR-modifying layer 94 may include a scaffold (not shown) and an MVTR-modifying composition. The MVTR-modifying layer 94 may be extended along an entire surface of the PSA layer 96. It is also contemplated (though not depicted) that the PSA layer 96 and backing layer 92 may extend beyond the periphery of the MVTR-modifying layer 94.

The backing layer 92 may be extruded directly onto the MVTR-modifying layer 94. The MVTR-modifying layer and backing layer construction may then be laminated directly onto the PSA layer 96. Exemplary methods of extrusion and laminating may be found in, for example, European Patent No. 1 255 575.

Figure 9:
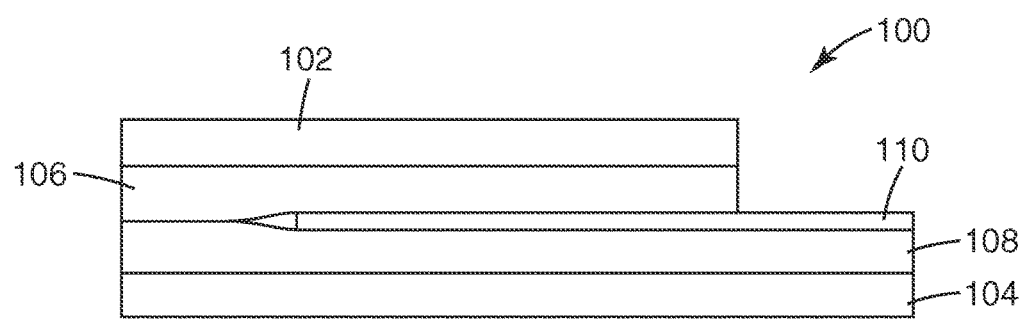
FIG. 9 is a side view of a medical article according to an embodiment of the present invention.

A further embodiment of the disclosure is depicted in FIG. 9. A wound wick 100 may include two backing layers (102, 104) operably attached to two PSA layers (106, 108). PSA layer 106 can be laminated or otherwise attached to PSA layer 108, such that the backing and PSA layers partially enclose an MVTR-modifying layer 110. The wound wick 100 features an exposed portion of the MVTR-modifying layer 110.

A further embodiment of the disclosure comprises a kit (not shown) including an MVTR-modifying layer, a PSA layer, and a backing layer. The MVTR-modifying layer may comprise a scaffold including MVTR-modifying material. The PSA layer may be provided laminated or otherwise affixed to the backing layer. The scaffold may be provided and/or packaged separately from the PSA and backing Preferably no portion of the scaffold is in contact with a surface of the PSA layer when packaged. The scaffold may be placed at any desired location on the surface of the PSA layer, on the surface of the backing layer, or proximate either. The size and shape of the scaffold may be modified if so desired. It is also contemplated that the MVTR-modifying composition may be provided separately (i.e., without a scaffold) so that it may be deposited, coated, or placed directly on a surface of the PSA layer by the practitioner.

Other components may also be added to the previous embodiments of the present invention without exceeding the scope of the present invention. For example, an absorbent layer may be disposed between the target site and the MVTR-modifying layer. The absorbent layer may include one or more layers of padding, including, but not limited to, polymeric films, gels, alginates, and foams. Exemplary absorbent foams are described in U.S. Pat. No. 6,548,727 (Swenson). In one embodiment, the absorbent layer comprises the foam used in the foam adhesive dressing available from 3M Company, St. Paul, Minn. under the trade name TEGADERM.

In an embodiment wherein the absorbent layer includes a pad, the absorbent pad is sometimes referred to as an "island pad" because the backing layer and PSA layer extends substantially beyond at least a portion of the periphery of the absorbent pad, and typically beyond the entire periphery of the absorbent pad. For example, the diameter of the absorbent pad can be, for example, 7.5 cm, while a backing for this pad can be 12.5 cm in diameter.

The backing layer can include a transparent elastic polymeric film (e.g., urethane) having a thickness not greater than 1 mm. The backing layer construction in this embodiment should be sufficiently stiff such that it will not fold over onto itself where it is not adequately supported by a support layer (such as further described below) or the absorbent pad. Portions of the backing layer can be as thin as 0.012 mm (12 microns).

Embodiments of the present invention may further include a support layer at least partially secured to the backing layer, for example, by heat seal bonding or with the use of an adhesive. The support layer allows for easier placement of the wound dressing on the patient. Examples of suitable support layers may be found in U.S. Pat. No. 6,838,589 (Liedtke et al.) and U.S. Pat. No. 5,738,642 (Heinecke et al.), and co-pending application Ser. No. 11/463,853 (Holm et al.)

Figure 10:
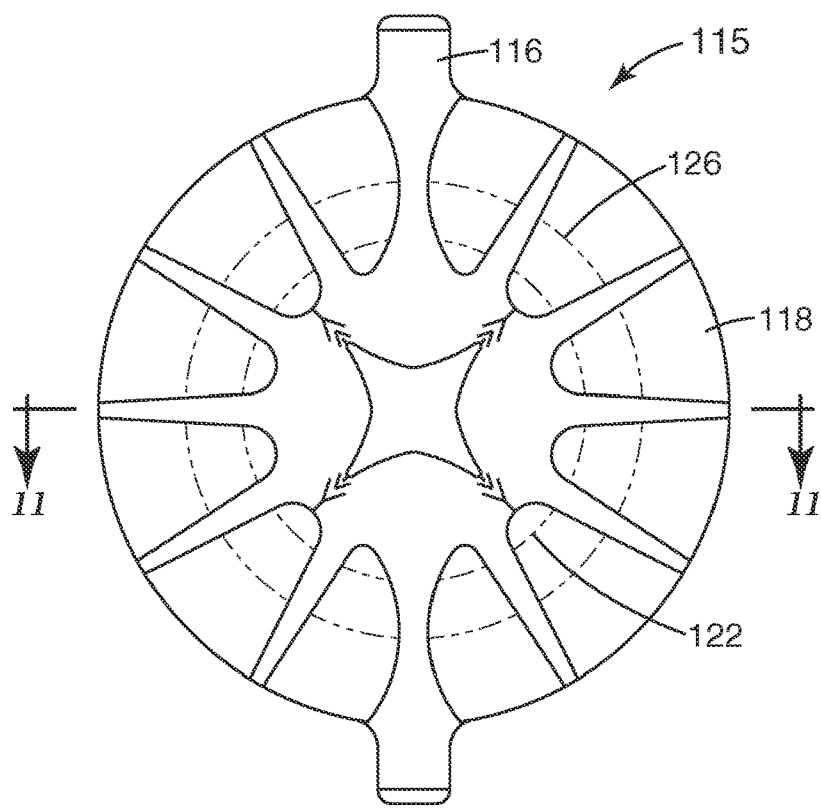
FIG. 10 is a top view of a wound dressing in a further embodiment of the present invention

In certain implementations of the invention the support layer has a substantially radial configuration as shown in FIG. 10, with a plurality of extensions radiating generally from the center of the dressing. The support layer forms a plurality of alternating uncovered portions of the adhesive backing layer, separated from one another by the extensions along the adhesive perimeter of the wound dressing. The support layer can be a single piece of material, such as a polymeric film, or can be two or more distinct pieces.

The medical articles of the present invention can also include a facing layer. The optional facing layer includes a facing substrate and a layer of facing adhesive on the target-site facing (e.g., wound-facing) surface of the facing layer. The facing layer is liquid permeable to, e.g., allow the passage of liquid wound exudate. The facing layer can include apertures formed through the facing layer to conduct exudate from the wound surface to the other layers. The apertures may be provided as slits, voids or other openings sufficiently large to provide for the passage of liquid through the facing layer.

A facing adhesive is optionally included to assist in securing the medical article to the patient. In one embodiment, the facing adhesive is substantially coextensive with the facing layer, i.e., the facing adhesive covers substantially the entire wound-facing surface of facing layer. In such constructions, it will be understood that the apertures would preferably extend though both the facing substrate and the facing adhesive. It will be understood, however, that facing adhesive may not be provided or may be provided on only a portion of the facing substrate. For example, the facing adhesive may be coated in a strip about the periphery of the facing substrate or pattern coated on the facing substrate. It is further contemplated that the facing layer and the facing adhesive may be coextensive with the backing layer and the PSA layer, with additional components disposed there between.

The medical articles of the present invention may also include a carrier film to protect the adhesive layer until the wound dressing is ready for use. To facilitate removal, the carrier film may have a tab which overhangs the end portion of the support layer. For example, the carrier film covers the surface of the medical article applied to the patient. The carrier film remains attached to the medical article until a user is ready to apply the dressing. The carrier film may be a single piece or multiple piece release liner, and may be part of or laminated to the package (not shown) containing the dressing, or merely enclosed along with the dressing within the package. The carrier film keeps the adhesive clean during storage and shipping of the wound dressing.

Figure 11:
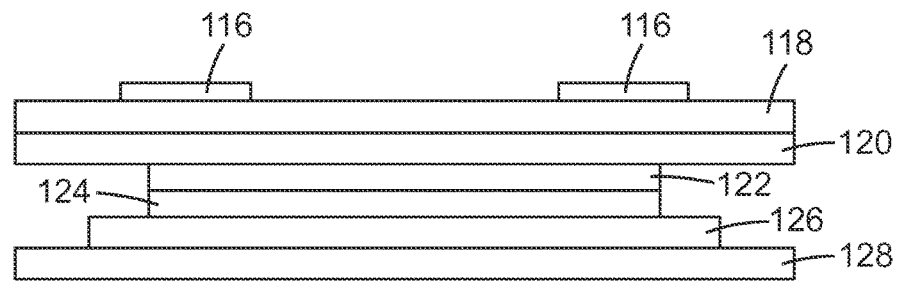
FIG. 11 is a cross-sectional view of the wound dressing of FIG. 10.

An exemplary wound dressing incorporating the carrier film, the support layer, and an absorbent layer is depicted in FIGS. 10 and 11. Wound dressing 115 includes a backing layer 118 with a first and second major surface. A PSA layer 120 is operably attached to the second major surface of the backing layer and a support layer 116 is disposed on the first major surface. An MVTR-modifying layer 122 is operably attached to a portion of the PSA layer 120. An absorbent layer including absorbent fabric 124 and absorbent foam 126 is disposed on the surface of the MVTR-modifying layer 122 opposite the PSA layer 120. As depicted, absorbent foam 126 extends beyond the periphery of the MVTR-modifying layer 118, but not to the periphery of the PSA layer 120. It is also contemplated that absorbent layer could be coextensive with the PSA layer 120. Carrier film 128 is positioned on the target site-facing (e.g., wound-facing) side of absorbent foam 126 and extends to the periphery of the PSA layer 120. Although not shown, the carrier film may be laminated to the PSA layer 120, such that absorbent layer and MVTR-modifying layer 122 are enclosed therebetween.

It is also contemplated, though not depicted, that wound dressing 110 may not include an MVTR-modifying layer, with MVTR-modifying composition instead directly deposited on the surface of the PSA layer prior to wound dressing construction. In such a construction, the absorbent fabric 120 can be operably attached directly to the PSA layer 116.

It is also contemplated that wound dressings of the present invention may be provided (i.e., packaged) in at least two components. In an embodiment that consists of those elements depicted in FIGS. 10 and 11, the first component may include the support layer, backing layer, PSA layer and a carrier film. The second component may include the MVTR-modifying layer and the absorbent layer. The first and second component may be packaged or otherwise provided separately, in that no portion of the MVTR-modifying layer is in contact with the PSA layer, or proximate thereto, until the at least two components are operatively attached. Other elements, such as pH-altering layers and filtration layers may be included in the components above without departing from the scope of the invention.

As one skilled in the art would appreciate, other implementations are appropriate in order to add or take away from the aspects the various embodiments of the wound dressings as described herein. For example, the backing layer can be multiple films or materials without diverging from the invention or deviating from the meaning of the term "film" as used herein. Similarly, the absorbent pad can include multiple sub-layers, including films, webs, sheets, etc. Also, additional layers and films of other materials can be added between the materials described herein without deviating from the invention.

Additional aspects of various components that may be employed in the invention will now be described in greater detail.

Support Layer

When a support layer is used, the material used to form the support layer is generally substantially more rigid than the backing layer to prevent the backing layer from improperly wrinkling during application to a patient. The support layer can be heat-sealable to the backing layer with or without a low adhesion coating as well known in the art. In general, the support layer materials can include, but are not limited to, polyethylene/vinyl acetate copolymer-coated papers and polyester films. One example of a suitable support layer material is a polyethylene/vinyl acetate copolymer coated super calendared Kraft paper (e.g., from Loparex of Dixon, Ill.).

The support layer can include perforations to aid in separating portions of the support layer after application of the dressing in a patient. Spacing and shape of the perforations are adjusted to give a support layer with relatively easy to tear performance on removal of the support layer from the applied dressing. The perforations may be shaped in accordance with any of the accepted perforation patterns including linear, angled, Y-shaped, V-shaped, dual-angled offset, sinusoidal, etc.

Exemplary embodiments of support layer constructions that may be used in the present invention are further described in U.S. Pat. No. 5,738,642 (Heinecke et al.), and U.S. Pat. No. 6,838,589 to Liedtke et al.

Backing Layer

The backing layer, also referred to herein as a backing, typically includes a liquid impervious, moisture vapor permeable polymeric film, although it can include a variety of other materials, which are preferably used in combination with a liquid impervious, moisture vapor permeable polymeric film. The liquid impervious, moisture vapor permeable polymeric film is a conformable organic polymeric material that preferably retains its structural integrity in a moist environment. Herein, "conformable" films are those that conform to a surface, even upon movement of the surface, as with the surface of a body part. Suitable films have a composition and thickness that allow for the passage of moisture vapor through them. The film aids in the regulation of water vapor loss from the wound area beneath the dressing. The film also acts as a barrier to both bacteria and to liquid water or other liquids.

The moisture vapor permeable polymeric films for use as backing layers in the present invention can be of a wide range of thicknesses. Preferably, they are at least 10 microns (micrometers) thick, and more preferably at least 12 microns thick. Preferably, they are no greater than 250 microns, and more preferably no greater than 75 microns thick. Furthermore, they can include one or more layers tailored to have the desired properties. These layers can be coextruded and/or bonded together with adhesive layers, for example, as long as the overall properties of the film and article, as described herein, are met.

Preferably, suitable films for use in the backing layer of the present invention have differential moisture vapor transmission properties. Preferably, a suitable film has a dry MVTR that is less than the wet MVTR of the film. Preferably, suitable films have a dry MVTR of at least 300 g/m²/24 hours and a wet MVTR of at least 3000 g/m²/24 hours. Preferably, the film has a wet MVTR greater 10,000 g/m²/24 hours, and more preferably greater than 15,000 g/m²/24 hours. The films can be tested using the same methods described above for the article.

Examples of suitable materials for the liquid-impervious, moisture-vapor permeable polymeric films of the backing layer include synthetic organic polymers including, but not limited to: polyurethanes commercially available from B.F. Goodrich, Cleveland, Ohio, under the trade designation ESTANE, including ESTANE 58237 and ESTANE 58245; polyetheramide block copolymers commercially available from Elf Atochem, Philadelphia, Pa., under the trade designation PEBAX, including PEBAX MV 1074; polyetherester block copolymers commercially available from DuPont, Wilmington, Del., under the trade designation HYTREL; and thermoplastic elastomers commercially available from DSM Engineering Plastics, Evansville, Ind., under the trade designation ARNITEL VT. The polymeric films can be made of one or more types of monomers (e.g., copolymers) or mixtures (e.g., blends) of polymers. Preferred materials are thermoplastic polymers, e.g., polymers that soften when exposed to heat and return to their original condition when cooled. A particularly preferred material is a thermoplastic polyurethane.

Backings of the medical articles of the present invention can also include other breathable materials including, for example, nonwoven, woven, and knit webs, porous films (e.g., provided by perforations or microporous structure), foams, paper, or other known backings A preferred backing includes a combination of a liquid-impervious, moisture-vapor permeable polymeric film and a moisture-vapor permeable nonwoven web that can, among other advantages, impart enhanced structural integrity and improved aesthetics to the dressings. These layers of film and web may or may not be coextensive. A preferred such nonwoven web is a melt processed polyurethane (such as that available under the trade designation MORTHANE PS-440 from Morton International, Seabrook, N.H.), or hydroentangled nonwoven polyester or rayon-polyester webs (such as those available under the trade designation SONTARA 8010 or SONTARA 8411 from DuPont, Wilmington, Del.).

A low adhesion coating (low adhesion backsize or LAB) can be provided on the backing layer on the side that may come into contact with the support layer. The low adhesion coating reduces the need to change the dressing due to unwanted dressing removal when other tapes or devices are placed on the dressing and removed, and reduces the surface friction of the dressing on linen or other fabrics, thereby offering additional protection against the accidental removal of dressing. A description of a low adhesion backing material suitable for use with the present invention can be found in U.S. Pat. Nos. 5,531,855 and 6,264,976.

Pressure Sensitive Adhesive

Various PSAs can be used to form adhesive layer 14 on the backing layer 12 to make it adhesive. For example, PSAs may be formulated to offer good skin adhesion characteristics, offer excellent conformability, and provide a gentle release from the skin and wound site. The PSA layer can be continuous, discontinuous, pattern coated, or melt-blown, for example.

One well known means of identifying PSAs is the Dahlquist criterion. This criterion defines a PSA as an adhesive having a 1 second creep compliance of greater than $1 \times 10^{-6}$ cm²/dyne as described in *Handbook of PSA Technology*, Donatas Satas (Ed.), $2^{nd}$ Edition, p. 172, Van Nostrand Reinhold, New York, N.Y., 1989. Alternatively, since modulus is, to a first approximation, the inverse of creep compliance, PSAs may be defined as adhesives having a Young's modulus of less than $1 \times 10^6$ dynes/cm². Another well known means of identifying a PSA is that it is aggressively and permanently tacky at room temperature and firmly adheres to a variety of dissimilar surfaces upon mere contact without the need of more than finger or hand pressure, and which may be removed from smooth surfaces without leaving a residue as described in *Glossary of Terms Used in the Pressure Sensitive Tape Industry* provided by the Pressure Sensitive Tape Council, 1996. Another suitable definition of a suitable PSA is that it preferably has a room temperature storage modulus within the area defined by the following points as plotted on a graph of modulus versus frequency at 25° C.: a range of moduli from approximately $2 \times 10^5$ to $4 \times 10^5$ dynes/cm² at a frequency of approximately 0.1 radians/sec (0.017 Hz), and a range of moduli from approximately $2 \times 10^6$ to $8 \times 10^6$ dynes/cm² at a frequency of approximately 100 radians/sec (17 Hz) (for example see FIG. 8-16 on p. 173 of *Handbook of PSA Technology* (Donatas Satas, Ed.), $2^{nd}$ Edition, Van Nostrand Rheinhold, New York, 1989). Any of these methods of identifying a PSA may be used to identify suitable PSAs for use in the methods of the present invention.

Examples of PSAs useful in the present invention include rubber based adhesives (e.g., tackified natural rubbers, synthetic rubbers, and styrene block copolymers), (meth)acrylics (i.e., (meth)acrylates), poly(alpha-olefins), polyurethanes, and silicones. Amine containing polymers can also be used which have amine groups in the backbone, pendant thereof, or combinations thereof. A suitable example includes a poly(ethyleneimine).

Some polymers may be chemically modified to include the desired amount of acid or base functionality. Alternatively, the polymers can be made with acid or base-functional monomers. Alternatively or additionally, the PSAs can include acid- or base-functional additives, such as tackifiers, plasticizers, or other additives.

Useful natural rubber PSAs generally contain masticated natural rubber, from 25 parts to 300 parts of one or more tackifying resins to 100 parts of natural rubber, and typically from 0.5 parts to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade. Tackifying resins used with natural rubbers generally include but are not limited to wood rosin and its hydrogenated derivatives; terpene resins of various softening points, and petroleum-based resins. Other materials can be added to natural rubber adhesives for special purposes, wherein the additions can include plasticizers, pigments, and curing agents to partially vulcanize the PSA. Examples of acid-modified tackifiers include acid-modified polyhydric alcohol rosin ester tackifiers as described in U.S. Pat. No. 5,120,781.

Another useful class of PSAs is those that include synthetic rubber. Such adhesives are generally rubbery elastomers, which are either self-tacky or non-tacky that require tackifiers. Examples of acid-modified tackifiers include acid-modified polyhydric alcohol rosin ester tackifiers as described in U.S. Pat. No. 5,120,781. Self-tacky synthetic rubber PSAs include for example, butyl rubber, a copolymer of isobutylene with less than 3 percent isoprene, polyisobutylene, a homopolymer of isoprene, polybutadiene, or styrene/butadiene rubber.

Synthetic rubber PSAs, that generally require tackifiers, are also usually easier to melt process. They include polybutadiene or styrene/butadiene rubber, from 10 parts to 200 parts of a tackifier, and generally from 0.5 parts to 2.0 parts per 100 parts rubber of an antioxidant. An example of a synthetic rubber is that available from BF Goodrich under the trade name AMERIPOL 101 IA, a styrene/butadiene rubber. Tackifiers that are useful include derivatives of rosins, polyterpenes, C5 aliphatic olefin-derived resins, and C9 aromatic/aliphatic olefin-derived resins.

Styrene block copolymer PSAs generally include elastomers of the A-B or A-B-A type, where A represents a thermoplastic polystyrene block and B represents a rubbery block of polyisoprene, polybutadiene, or poly(ethylene/butylene), and resins. Examples of the various block copolymers useful in block copolymer PSAs include linear, radial, star and tapered styrene-isoprene block copolymers such as those available under the trade names KRATON D 1107P, KRATON G1657, KRATON G 1750X, and KRATON D 1118X from Shell Chemical Co. The polystyrene blocks tend to form domains in the shape of spheroids, cylinders, or plates that causes the block copolymer PSAs to have two phase structures. Resins that associate with the rubber phase generally develop tack in the PSA. Examples of rubber phase associating resins include aliphatic olefin-derived resins, such as those available under the trade names ESCOREZ 1300 and WINGTACK from Goodyear; rosin esters, such as those available under the trade names FORAL and STAYBELITE Ester 10 from Hercules, Inc.; hydrogenated hydrocarbons, such as those available under the trade name ESCOREZ 5000 from Exxon; polyterpenes, such as those available under the trade name PICCOLYTE A; and terpene phenolic resins derived from petroleum or turpentine sources, such as those available under the trade name PICCOFYN A100 from Hercules, Inc. Resins that associate with the thermoplastic phase tend to stiffen the PSA.

In preferred PSAs of the present invention, acrylate and methacrylate monomers and polymers can be used and are referred to collectively herein as "(meth)acrylate" or "(meth)acrylic" monomers and polymers. (Meth)acrylate polymers may be copolymers, optionally in combination with other, non-(meth)acrylate, e.g., vinyl-unsaturated, monomers. Such polymers and their monomers are well-known in the polymer and adhesive arts, as are methods of preparing the monomers and polymers. One of skill will understand and recognize that such polymers can be useful to impart adhesive properties, and will understand their use in providing an adhesive as described herein.

(Meth)acrylic PSAs generally have a glass transition temperature of about −20° C. or less and may include from 100 to 60 weight percent of a C4-C12 alkyl ester component such as, for example, isooctyl acrylate, 2-ethyl-hexyl acrylate and n-butyl acrylate and from 0 to 40 weight percent of a polar component such as, for example, acrylic acid, methacrylic acid, ethylene, vinyl acetate, N-vinyl pyrrolidone and styrene macromer.

Suitable acidic monomers for preparing (meth)acrylic PSAs include those containing carboxylic acid functionality such as acrylic acid, methacrylic acid, itaconic acid, and the like; those containing sulfonic acid functionality such as 2-sulfoethyl methacrylate; and those containing phosphonic acid functionality. Preferred acidic monomers include acrylic acid and methacrylic acid.

Additional useful acidic monomers in the acidic copolymer include, but are not limited to, those selected from ethylenically unsaturated carboxylic acids, ethylenically unsaturated sulfonic acids, ethylenically unsaturated phosphonic acids, and mixtures thereof. Examples of such compounds include those selected from acrylic acid, methacrylic acid, itaconic acid, fumaric acid, crotonic acid, citraconic acid, maleic acid, oleic acid, B-carboxyethyl acrylate, 2-sulfoethyl methacrylate, styrene sulfonic acid, 2-acrylamido-2-methylpropane sulfonic acid, vinyl phosphonic acid, and the like, and mixtures thereof.

Due to their availability, acidic monomers of the present invention are typically the ethylenically unsaturated carboxylic acids. When even stronger acids are desired, acidic monomers include the ethylenically unsaturated sulfonic acids and ethylenically unsaturated phosphonic acids. Sulfonic and phosphonic acids generally provide a stronger interaction with a basic polymer. This stronger interaction can lead to greater improvements in cohesive strength, as well as higher temperature resistance and solvent resistance of the adhesive.

Suitable basic monomers for preparing (meth)acrylic PSAs include those containing amine functionality such as vinyl pyridine, N,N-diethylaminoethyl methacrylate, N,N-dimethylamino-ethyl methacrylate, N,N-diethylaminoethyl acrylate, N,N-dimethylaminoethyl acrylate, and N-t-butylaminoethyl methacrylate. Preferred basic monomers include N,N-dimethylaminoethyl methacrylate, and N,N-dimethylaminoethyl acrylate.

The (meth)acrylic PSAs may be self-tacky or tackified. Useful tackifiers for (meth)acrylics are rosin esters such as that available under the trade name FORAL 85 from Hercules, Inc., aromatic resins such as that available under the trade name PICCOTEX LC-55WK from Hercules, Inc., aliphatic resins such as that available under the trade name PICCOTAC 95 from Hercules, Inc., and terpene resins such as that available under the trade names PICCOLYTE A-115 and ZONAREZ B-100 from Arizona Chemical Co. Other materials can be added for special purposes, including hydrogenated butyl rubber, pigments, and curing agents to vulcanize the adhesive partially. Examples of acid-modified tackifiers include acid-modified polyhydric alcohol rosin ester tackifiers as described in U.S. Pat. No. 5,120,781.

Poly(alpha-olefin) PSAs, also called a poly(l-alkene) PSAs, generally include either a substantially uncrosslinked polymer or a uncrosslinked polymer that may have radiation activatable functional groups grafted thereon as described in U.S. Pat. No. 5,209,971 (Babu, et al.). The poly(alpha-olefin) polymer may include one or more tackifying materials, not only to improve adhesive properties but also provide the necessary acidic or basic functional groups needed for this application. Tackifying materials are typically resins that are miscible in the poly(alpha-olefin) polymer. The total amount of tackifying resin in the poly(alpha-olefin) polymer ranges from 0 to 150 parts by weight per 100 parts of the poly(alpha-olefin) polymer depending on the specific application. Useful tackifying resins include resins derived by polymerization of C5 to C9 unsaturated hydrocarbon monomers, polyterpenes, synthetic polyterpenes and the like. Examples of such commercially available resins based on a C5 olefin fraction of this type include those available under the trade name WINGTACK from Goodyear Tire and Rubber Co. Other materials can be added for special purposes, including antioxidants, fillers, pigments, and radiation activated crosslinking agents.

Another useful class of PSAs can include polyurethanes. Polyurethanes may be produced by reacting a polyisocyanate with a polyalcohol (polyol). As described herein, a polyisocyanate is a molecule with two or more isocyanate functional groups and a polyalcohol is a molecule with two or more hydroxyl functional groups. The reaction product is a polymer containing urethane linkages. The functional groups can be alkanes, esters, ethers, and other components.

Isocyanates can be classed as aromatic, such as diphenylmethane diisocyanate (MDI) or toluene diisocyanate (TDI); or aliphatic, such as hexamethylene diisocyanate (HDI) or isophorone diisocyanate (IPDI). An example of a polymeric isocyanate is polymeric diphenylmethane diisocyanate, which is a blend of molecules with two-, three-, and four- or more isocyanate groups, with an average functionality of 2.7. Isocyanates can be further modified by partially reacting them with a polyol to form a prepolymer. A quasi-prepolymer is formed when the stoichiometric ratio of isocyanate to hydroxyl groups is greater than 2:1. A true prepolymer is formed when the stoichiometric ratio is equal to 2:1. Important characteristics of isocyanates include the molecular backbone, % NCO content, functionality, and viscosity.

Polyols are distinguished from short chain or low-molecular weight glycol chain extenders and cross linkers such as ethylene glycol (EG), 1,4-butanediol (BDO), diethylene glycol (DEG), glycerine, and trimethylol propane (TMP). Polyols are formed by base-catalyzed addition of propylene oxide (PO), ethylene oxide (EO) onto a hydroxyl or amine containing initiator, or by polyesterification of a di-acid, such as adipic acid, with glycols, such as ethylene glycol or dipropylene glycol (DPG). The choice of initiator, extender, and molecular weight of the polyol greatly affect its physical state, and the physical properties of the polyurethane polymer. Important characteristics of polyols include the molecular backbone, initiator, molecular weight, % primary hydroxyl groups, functionality, and viscosity. Examples of suitable polyurethanes adhesives include those in U.S. Pat. No. 7,160,976 (Luhmann, et al.), U.S. Pat. No. 6,642,304 (Hansen, et. al), and U.S. Pat. No. 6,518,359 (Clemens et al.).

Silicone PSAs include two major components, a polymer or gum, and a tackifying resin. The polymer is typically a high molecular weight polydimethylsiloxane or polydimethyldiphenylsiloxane, that contains residual silanol functionality (SiOH) on the ends of the polymer chain, or a block copolymer including polydiorganosiloxane soft segments and urea terminated hard segments. The tackifying resin is generally a three-dimensional silicate structure that is end-capped with trimethylsiloxy groups ($OSiMe_3$) and also contains some residual silanol functionality. Examples of tackifying resins include SR 545, from General Electric Co., Silicone Resins Division, Waterford, N.Y., and MQD-32-2 from Shin-Etsu Silicones of America, Inc., Torrance, Calif. Manufacture of typical silicone PSAs is described in U.S. Pat. No. 2,736,721 (Dexter). Manufacture of silicone urea block copolymer PSA is described in U.S. Pat. No. 5,214,119 (Leir et al.).

In some embodiments, the adhesive contains greater than 0.42 mmoles of acidic- or basic-functional groups per gram of PSA that can be neutralized by the MVTR-modifying material. More preferably, the adhesive contains at least 0.69 mmoles of these functional groups per gram of PSA. Even more preferably, the adhesive contains 0.84 mmoles of these functional groups. Even more preferably, the adhesive contains at least 1.3 mmoles of these functional groups. Even more preferably, the adhesive contains at least 1.80 mmoles of these functional groups. Even more preferably, the adhesive contains at least 2.08 mmoles of these functional groups. In most embodiments, the adhesive contains between 1.3 mmoles and 2.5 mmoles of these functional groups.

Preferably, the adhesive should contain no greater than 5.6 mmoles of these functional groups per gram of PSA. More preferably, the adhesive contains no greater than 4.2 mmoles of these functional groups per gram of PSA, and even more preferably no greater than 2.8 mmoles of these functional groups per gram of PSA.

In some embodiments wherein the PSA contains a polymer formed from acidic monomers, the corresponding weight percents may be considered. Preferably, the PSA contains greater than 3 weight percent of a monomer unit in the adhesive polymer that contains acid/base functional groups that can be neutralized by the MVTR-modifying material. More preferably, the PSA contains at least 6 weight percent of these functionalized monomer units. Even more preferably, the PSA contains at least 9 weight percent of these functionalized monomer units. Even more preferably, the PSA contains at least 10 weight percent of these functionalized monomer units. Even more preferably, the PSA contains at least 12 weight percent of these functionalized monomer units. Preferably, the PSA should contain no greater than 40 weight percent of the functionalized monomer units. More preferably the PSA contains no greater than 30 weight percent, even more preferably no greater than 25 weight percent of the functionalized monomer units, and most preferably no greater than 20 based on the total weight of the monomers used in the polymer used to make the PSA. Preferably, such values apply to (meth)acrylate polymers.

In certain embodiments, the PSA may include additional hydrophilic polymer components. These hydrophilic polymer components of the PSA are distinct from plasticizers or other additives that may be used in the adhesive to tackify or otherwise affect properties of the adhesive. The hydrophilic polymer component may be reactive or nonreactive with the adhesive monomers in the PSA. If the hydrophilic polymer is nonreactive (i.e., not incorporated into the polymer chain) the molecular weight of the hydrophilic polymer component is greater than 1000. More preferably, the molecular weight is greater than 2000.

When present in the adhesive, the hydrophilic polymer components are generally present in amounts no greater than 30 weight percent, based on the total weight of the PSA. In those adhesives that include a hydrophilic polymer component, lower concentrations of acid- or basic-functional groups in the PSA may be needed to impact a significant increase in MVTR when an MVTR-modifying material is incorporated into a medical article including the PSA, in comparison to a PSA of the same mass concentration of acid- or basic-functional groups that does not include the hydrophilic polymer components. For example, a PSA with 10 weight percent acid functional groups and 10 weight percent of additional hydrophilic component(s) may show a greater increase in MVTR when exposed to an appropriate MVTR-modifying material by comparison to a PSA with only 10 weight percent acid functional groups and no additional hydrophilic components. The combined weight percent of reactive groups (e.g., acid) and hydrophilic polymer components in the PSA is preferably at least 15%, more preferably at least 20%, and most preferably at least 24% by weight of the PSA. For example, if the adhesive contains 6% acid groups, then the hydrophilic component should be at least 9% by weight, more preferably at least 14% by weight, and most preferably at least 18% by weight. If the adhesive group contains 12 weight % acrylic acid, the hydrophilic component should be at least 3% by weight, more preferably at least 8% by weight, and most preferably at least 12% by weight of the PSA.

In certain embodiments, the ratio of the hydrophobic polymer component(s) in the PSA to the hydrophilic polymer component(s) in the PSA is preferably at least 1.5:1. More preferably at least 1.9:1, even more preferably 2.3:1. In most embodiments, less than 6:1.

In certain embodiments, an exemplary nonreactive hydrophilic polymer component includes one or more poly(alkylene oxide) copolymers. The poly(alkylene oxide) copolymers can be combined with the PSA monomers (e.g., (meth)acrylate monomers or other acidic monomers) or with the copolymer formed from the PSA monomers. The poly(alkylene oxide) copolymers generally do not migrate to the extent of phase separation between the copolymerized acrylate monomers and the poly(alkylene oxide) copolymer. By "phase separation" or "phase separate," it is meant that visible crystallization or liquid regions do not appear in the adhesive solution or bulk adhesive.

In preferred embodiments, the poly(alkylene oxide) copolymers include at least two copolymerized alkylene oxide monomers, at least one of which is hydrophilic and at least one of which is hydrophobic. A preferred copolymer is formed from ethylene oxide and propylene oxide. They can be random, alternating, or block. Preferably, they are block copolymers that include hydrophobic and hydrophilic segments. Particularly useful poly(alkylene oxide) copolymers have a weight average molecular weight of about 1000 to about 15,000, preferably of about 3000 to about 12,000.

Preferred poly(alkylene oxide) copolymers have appreciable water solubility, preferably, at least about 10 parts per 100 parts of water, exhibit surfactant characteristics preferably having an HLB (hydrophilic lipophilic balance) value of about 3 to about 15, and more preferably, about 5 to about 12. Useful poly(alkylene oxide) copolymers have ratios of hydrophilic monomers (e.g., ethylene oxide) to hydrophobic monomers (e.g., propylene oxide) of from about 90:10 to about 10:90, more preferably, from about 80:20 to about 30:70.

Monomers that may be used to make poly(alkylene oxide) copolymers include ethylene oxide and related glycols as a hydrophilic component and propylene oxide, butylene oxide, trimethylene oxide, tetramethylene oxide and the like and related glycols as a hydrophobic component. The poly(alkylene oxide) copolymers may be terminated with lower alkyl groups, amino groups, hydroxyl groups, carboxylic acid groups, aromatic groups, or other nonreactive groups.

Examples of useful poly(alkylene oxide) copolymers include, but are not limited to, those poly(alkylene oxide) copolymers available under the trade designations TETRONIC (tetrafunctional block copolymers derived from sequential addition of propylene oxide and ethylene oxide to ethylene diamine with hydrophilic endblocks) and TETRONIC R (tetrafunctional block copolymers derived from sequential addition of propylene oxide and ethylene oxide to ethylene diamine with hydrophobic endblocks) copolymers available from BASF, Mt. Olive, N.J.; PLURONIC (triblock copolymers with poly(ethylene oxide) end blocks and poly(propylene oxide) midblock) and PLURONIC R (triblock copolymers with poly(propylene oxide) endblocks and poly(ethylene oxide) midblock) copolymers available from BASF; UCON Fluids (random copolymers of ethylene oxide and propylene oxide) available from Union Carbide, Danbury, Conn. Various combinations of poly(alkylene oxide) copolymers can also be used. Preferred nonreactive hydrophilic polymer components are block copolymers of polyethylene glycol and propylene glycol available from BASF, Germany under the trade name PLURONIC.

Preferably, the poly(alkylene oxide) copolymer can be used in an amount of at least about 5 weight percent (wt-%), based on the total weight of the adhesive composition (e.g., the copolymerized (meth)acrylate/hydrophilic acidic comonomers and poly(alkylene oxide) copolymer). More preferably, the poly(alkylene oxide) copolymer is used in an amount of at least about 10 wt-%, and most preferably, at least about 15 wt-%. Preferably, the poly(alkylene oxide) copolymer can be used in an amount of no greater than about 30 wt-%. The amount of poly(alkylene oxide) copolymer required depends upon the type and ratios of the (meth)acrylate and hydrophilic acidic comonomers employed in the polymerizable mixture and the type and molecular weight of the poly(alkylene oxide) copolymer used in the adhesive composition.

In other embodiments, an exemplary reactive hydrophilic polymer component includes a hydrophilic macromolecular monomer which has a vinyl group copolymerizable with the PSA monomers. The hydrophilic macromolecular monomer contains a plurality of hydrophilic sites which impart the required hydrophilicity to the monomer. The hydrophilic macromolecular monomer may be represented by the general Formula I

X—Y—Z wherein X is a vinyl group copolymerizable with the PSA monomers, Y is a divalent linking group, and Z is a monovalent polymeric moiety, i.e., containing two or more monomer units, comprising a polyether essentially unreactive under the free radical initiated, copolymerizing conditions employed to form the pressure-sensitive adhesive terpolymer.

The preferred X group is of the general Formula II:

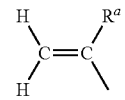

wherein $R^a$ is a hydrogen atom or a methyl group.

The preferred Y group is a

group (i.e., a divalent carbonyl group).

The preferred Z moiety is a monovalent polyether of the general formula III

—W—$OR^b$ wherein $R^b$ is hydrogen, lower alkyl, phenyl, or substituted phenyl; and W is a divalent poly(lower alkylene oxide) group containing 2 to about 250 repeating alkoxy units and selected from the group consisting of a poly(ethylene oxide) radical, a polypropylene oxide) radical, a radical of a copolymer of ethylene oxide and propylene oxide, and a poly(tetramethylene oxide) radical. In a preferred hydrophilic macromonomer, a monovalent polyether of Formula III is bonded covalently to the carbonyl group (i.e., where Y is divalent carbonyl) through a terminal oxygen atom contained in the W moiety.

A variety of hydrophilic macromolecular monomers are available commercially. For example, commercially available monomers which have been found to be suitable are the 2-(2-ethoxyethoxy)ethyl acrylate which is available under the trade designation "SR-256" from Sartomer Company, West Chester, Pa.; the methoxy poly(ethylene oxide) acrylate which is available under the trade designation "No. 8816" from Monomer-Polymer & Dajac Laboratories, Inc., Trevose, Pa.; the methoxy poly(ethylene oxide) methacrylates of 200 Daltons, 400 Daltons, and 1000 Daltons which are available under the trade designations "No. 16664", "No. 16665" and "No. 16666", respectively, from Polysciences, Inc., Warrington, Pa.; and the hydroxy poly(ethylene oxide) methacrylate which is available under the trade designation "No. 16712" from Polysciences, Inc., Warrington, Pa.

Other preferred hydrophilic macromolecular monomers may be prepared using commercially available starting materials and conventional methods, for example, as described in U.S. Pat. No. 4,871,812.

In general, the hydrophilic macromolecular monomer is present in an amount of about 5 to 30% of the total weight of all monomers in the terpolymer. Preferred amounts for the monomers are about 10 to 20% by weight based upon the total amount of all monomers in the terpolymer.

Preferred polymers included in the PSA are (meth)acrylate polymers. Particularly useful adhesive compositions include a 65:15:20 2-ethylhexylacrylate:acrylic acid:copolymer blended with a nonreactive polyakylene oxide copolymer under the name PLURONIC. Other suitable examples include a 90:10 iso-octyl acrylate:acrylic acid copolymer, a 70:15:15 isooctyl acrylate:ethyleneoxide acrylate:acrylic acid terpolymer, and a 25:69:6 2-ethylhexylacrylate:butyl acrylate:acrylic acid terpolymer. Useful adhesives can be any of those that are compatible with skin and useful for wound dressings, such as those disclosed in U.S. Pat. No. Re. 24,906 (Ulrich), U.S. Pat. No. 5,849,325 (Heinecke, et al.), and U.S. Pat. No. 4,871,812 (Lucast, et. al.) (water-based and solvent-based adhesives); U.S. Pat. No. 4,833,179 (Young, et al.) (hot-melt adhesives); U.S. Pat. No. 5,908,693 (Delgado, et al.) (microsphere adhesives); U.S. Pat. Nos. 6,171,985 and 6,083,856 (both to Joseph, et al.) (low trauma fibrous adhesives); and, U.S. Pat. No. 6,198,016 (Lucast, et al.), U.S. Pat. No. 6,518,343 (Lucast, et al.), and U.S. Pat. No. 6,441,082 (Gieselman) (wet-skin adhesives). Inclusion of medicaments or antimicrobial agents in the adhesive is also contemplated, as described in U.S. Pat. Nos. 4,310,509 and 4,323,557.

Scaffold

When used, the scaffold 22, as shown, for example, in FIG. 2, may include a nonwoven material. Suitable nonwoven materials include, but are not limited to, TENCEL/Polyester nonwovens, and Lycocell-Rayon/Polyester Nonwovens both available from Ahlstrom Green Bay, Green Bay, Wis. Other suitable nonwovens include cotton spun laced nonwovens available from Unitika Ltd., Japan. In another embodiment, the scaffold 22 is a TMED011 nonwoven available from National Nonwovens Co., East Hampton, Mass. The scaffold 22 may also include wovens, knitted fabrics, foams, porous films, gels, hydrocolloids, cellulosic material, carboxyl methyl cellulose, alginates, and water-swellable or water-absorbable adhesives. In preferred embodiments, the scaffold 22 is capable of absorbing moisture.

Filtration Layer

When used, the filtration layer 32, as shown for example in FIG. 3b, may include one or more nonwoven layers. Suitable nonwoven materials include, but are not limited to, TENCEL/Polyester nonwovens, and Lycocell-Rayon/Polyester Nonwovens both available from Ahlstrom Green Bay, Green Bay, Wis. Other suitable nonwovens include cotton spun laced nonwovens available from Unitika Ltd., Japan. In another embodiment, the filtration layer 32 is a TMED011 nonwoven available from National Nonwovens Co., East Hampton, Mass. The filtration layer may also be composed of wovens, knitted fabrics, foams, porous films, gels, hydrocolloids, cellulosic material, alginates, porous adhesives (hydrophobic or hydrophilic), and water-swellable or water-absorbable adhesives.

Suitable examples of a filtration layer selected for filtration purposes include filtration membranes, filtration materials, non wovens, wovens, gels and foams.

Absorbent Layer

When used, the absorbent layer can be manufactured of any of a variety of materials including, but not limited to, woven or nonwoven cotton or rayon. Absorbent layer is useful for containing a number of substances, optionally including antimicrobial agents, drugs for transdermal drug delivery, chemical indicators to monitor hormones or other substances in a patient, etc.

The absorbent layer may include a hydrocolloid composition, including the hydrocolloid compositions described in U.S. Pat. Nos. 5,622,711 and 5,633,010. Absorbent materials may also be chosen from other synthetic and natural materials including polymer gels, foams, collagens, carboxymethyl cellulose fibers, alginates, nonwovens, or woven materials. In some embodiments, the absorbent layer may include a polymeric fabric, a polymeric foam, and combinations thereof. For example, the polymeric fabric may be a nonwoven and the polymeric foam may be the foam used in the TEGADERM foam adhesive dressing available from 3M Company, St. Paul, Minn. In certain embodiments, the polymeric foam is a polyurethane foam.

Facing Layer

When used, the facing layer is preferably soft, flexible, conformable, non-irritating and non-sensitizing. Any of a variety of polymers may be used including polyurethane, polyethylene, polypropylene, polyamide or polyester materials. Further, the facing layer may be in the form of moisture vapor permeable films, perforated films, woven-, non-woven or knit webs or scrims.

The facing layer may also include an adhesive laminated on the surface of the filtration layer facing the wound or other target site. In such an embodiment, the second adhesive may be an acrylic, silicone gel, polyurethane, or rubber based adhesive. Exemplary embodiments of suitable facing layers and adhesives may be found, for example, in U.S. Pat. No. 7,612,248 to Burton et al. The facing layer may also include an additional adhesive on the surface of the facing layer opposite the target site.

Carrier Films

Carrier films (e.g., as shown in FIG. 11) suitable for use with the invention can be made of kraft papers, polyethylene, polypropylene, polyester or composites of any of these materials. The films are preferably coated with release agents such as fluorochemicals or silicones. For example, U.S. Pat. No. 4,472,480 describes low surface energy perfluorochemical liners. The liners are papers, polyolefin films, or polyester films coated with silicone release materials. Examples of commercially available silicone coated release papers are POLYSILK™, silicone release papers available from Rexam Release (Bedford Park, Ill.) and silicone release papers supplied by Loparex Inc. (Willowbrook, Ill.).

Objects and advantages of this invention are further illustrated by the following examples, but the particular materials and amounts thereof recited in these examples, as well as other conditions and details, should not be construed to unduly limit this invention. Unless otherwise indicated, all parts and percentages are by weight.

EXAMPLES

TABLE 1

Glossary of Components

| Material/Trade Name | Description | Source/Address |
|---|---|---|
| 3M TEGADERM 9548HP | Transparent Film Dressing | 3M Company, St. Paul, MN |
| 3M TEGADERM 90612 | Foam Adhesive Dressing | 3M Company, St. Paul, MN |
| ESTANE 58237 Resin | Polyurethane resin | Lubrizol, Wickliffe, OH |
| 70/30 TENCEL/Polyester Non-woven | Grade 240 (SX-33) spunlaced non-woven, 40 g/m², 24 mesh apertured; 70/30 TENCEL/polyester | Ahlstrom, Green Bay, WI |
| 30/70 Lycocell-Rayon/Polyester Non-woven | Grade SX-473 spunlaced, non-apertured non-woven, 45 g/m² | Ahlstrom, Green Bay, WI Invention |
| COTTOASE | 100% cotton, spunlaced non-woven, 50 gsm | Unitika, Japan |
| Water | USP Sterile water | Baxter, Deerfield, IL |
| $Na_2CO_3$—$H_2O$ | Sodium carbonate monohydrate | Mallinckrodt, Phillipsburg, NJ or Fisher Scientific, Fair Lawn, NJ |
| $CH_3N(C_2H_4OH)_2$ | Methyl diethanolamine (MDEA) | Dow, Midland, MI |
| $C_3H_5(OH)_3$ | Glycerol, USP grade | J. T. Baker, Phillipsburg, NJ |
| Polyethylene glycol 400 | PEG 400, Ph Eur grade | EMD Chemicals, Gibbstown, NJ |

Test Methods

1. Moisture Vapor Transmission Rate—Upright (Dry) MVTR

A. For Samples That Did Not Contain a Foam Component

The upright MVTR was measured according to ASTM E-96-80 using a modified Payne cup method. A 3.8 cm diameter sample was placed between adhesive-containing surfaces of two foil adhesive rings, each having a 5.1 cm² elliptical opening. The holes of each ring were carefully aligned. Finger pressure was used to form a foil/sample/foil assembly that was flat, wrinkle free, and had no void areas in the exposed sample.

A 120-ml glass jar was filled with approximately 50 g of tap water that contained a couple drops of 0.02% (w/w) aqueous Methylene Blue USP (Basic Blue 9, C.I.52015) solution, unless specifically stated in an example. The jar was fitted with a screw-on cap having a 3.8 cm diameter hole in the center thereof and with a 4.45 cm diameter rubber washer having an approximately 3.6 cm hole in its center The rubber washer was placed on the lip of the jar and foil/sample/foil assembly was placed backing side down on the rubber washer. The lid was then screwed loosely on the jar.

The assembly was placed in a chamber at 40° C. and 20% relative humidity for four hours. At the end of four hours, the cap was tightened inside the chamber so that the sample was level with the cap (no bulging) and the rubber washer was in proper seating position.

The foil sample assembly was removed from the chamber and weighed immediately to the nearest 0.01 gram for an initial dry weight, W1. The assembly was then returned to the chamber for at least 18 hours, the exposure time T1 in hours, after which it was removed and weighed immediately to the nearest 0.01 g for a final dry weight, W2. The MVTR in grams of water vapor transmitted per square meter of sample area per 24 hours can then be calculated using the following formula.

$$\text{Upright (Dry) MVTR} = (W1-W2) \times (4.74 \times 10^4)/T1$$

B. For Samples That Did Contain a Foam Component

The upright MVTR procedure for these samples was identical to that described above except the test sample size was a 4.45 cm diameter sample and the sample was sandwich between two LEXAN (polycarbonate) washers (4.47 cm diameter with 2.54 cm hole in the middle), instead of the foil adhesive rings.

2. Moisture Vapor Transmission Rate—Inverted (Wet) MVTR

The inverted MVTR was measured using the following test procedure. After obtaining the final "dry" weight, W2, as described for the upright MVTR procedures, the assembly was returned to the chamber for a least 18 additional hours of exposure time, T2, with the jars inverted so that the tap water was in direct contact with the test sample. The sample was then removed from the chamber and weighed to the nearest 0.01 gram for a final wet weight, W3. The inverted wet MVTR in grams of water vapor transmitted per square meter of sample area per 24 hours can then be calculated using the following formula.

$$\text{Inverted (Wet) MVTR} = (W2-W3) \times (4.74 \times 10^4)/T2$$

Multiple samples of the Examples below were measured for Upright (Dry) and Inverted (Wet) MVTR. The average results are reported below, followed by the standard deviation (+/−) of the multiple samples.

3. Adhesion to Steel

The Adhesion to Steel test was performed in accordance with ASTM D3330M at 30.5 cm/min and 180 degree peel.

Example 1 (Comparative)

A 40 g/m² 70/30 (w/w) TENCEL/Polyester Grade 240 (SX-33) spunlaced non-woven (Ahlstrom Green Bay, Green Bay, Wis.) was laminated by hand to the adhesive side of a 3M TEGADERM 9548HP dressing and allowed to sit for approximately 30 days prior to testing. Five specimens from the sample were tested for both upright and inverted Moisture Vapor Transmission Rates (MVTR). The average upright MVTR and inverted MVTR values were 1150+/−100 g/m$^2$/24 hours and 2340+/−190 g/m$^2$/24 hours, respectively.

Example 2 (Comparative)

The non-woven from Example 1 was saturated with a 2.6% (w/w) aqueous solution of sodium citrate dehydrate and dried in a laboratory scale forced air oven (Memmert Universal Oven; Wisconsin Oven Company, East Troy, Wis.) at 80° C. for 30 minutes. The coating weight of sodium citrate dehydrate on the non-woven was 15 g/m$^2$. This coated non-woven was then laminated by hand to the adhesive side of a 3M TEGADERM 9548HP dressing. Samples were allowed to sit for approximately 30 days prior to testing. For the five specimens tested from the sample, the average upright MVTR and inverted MVTR values were 1000+/−30 g/m$^2$/24 hours and 2350+/−90 g/m$^2$/24 hours, respectively.

Example 3 (Comparative)

A 100% cotton spunlaced non-woven (COTTOASE) was saturated with a 5.4% (w/w) aqueous solution of citric acid, dried in an oven at 85° C. for approximately 30 minutes, and then laminated by hand to the adhesive side of a 3M TEGADERM 9548HP dressing. The samples were allowed to sit for 3 days prior to testing. The average upright MVTR and inverted MVTR values for the four test specimens were 1180+/−60 g/m$^2$/24 hours and 1720+/−40 g/m$^2$/24 hours, respectively.

Example 4 (Comparative)

The non-woven from Example 1 was saturated with a 3.5% (w/w) aqueous solution of sodium carbonate monohydrate at a rate of 13 feet/min (3.96 meter/min) and dried in a pilot scale forced air oven at approximately 105° C. for about 5 minutes. The coating weight of sodium carbonate monohydrate on the non-woven was 16.3 g/m$^2$. This coated non-woven was then laminated by hand to the adhesive side of a 3M TEGADERM 9548HP dressing. The average upright MVTR and inverted MVTR values of five test specimens were 1070+/−40 g/m$^2$/24 hours and 20800+/−980 g/m$^2$/24 hours, respectively.

Example 5

The non-woven from Example 1 was saturated with a 2% (w/w) aqueous solution of methyl diethanolamine (MDEA), and then dried in an oven at 75° C. for 30 minutes. The coating weight of MDEA on the non-woven was 6 g/m$^2$. This coated non-woven was then laminated by hand to the adhesive side of a 3M TEGADERM 9548HP dressing. The samples were tested approximately nine days after the lamination step. The average upright MVTR and inverted MVTR values of four test specimens were 2160+/−80 g/m$^2$/24 hours and 19800+/−940 g/m$^2$/24 hours, respectively.

Example 6 (Comparative)

The non-woven from Example 1 was saturated with a 5% (w/w) aqueous solution of polyethylene glycol 400, and then dried in an oven at 80° C. for 30 minutes. The coating weight of MDEA on the non-woven was 31 g/m$^2$. This coated non-woven was then laminated by hand to the adhesive side of a 3M TEGADERM 9548HP dressing. The samples were tested five days after the lamination step. The average upright MVTR and inverted MVTR values of four test specimens were 1530+/−50 g/m$^2$/24 hours and 2290+/−90 g/m$^2$/24 hours, respectively.

Example 7 (Comparative)

For this example, an approximately 25 micron thick adhesive on paper liner as described in U.S. Pat. No. 4,737,410 Example 31 with less than 1% polyethyloxazoline was used in this example. An approximately 25 micron urethane film (ESTANE 58237 resin; Lubrizol Corporation, Wickliffe, Ohio) was extruded over the aforementioned adhesive layer using the method as described in U.S. Pat. No. 4,499,896 to form the adhesive/film laminate on liner. The non-woven from Example 1, a 40 g/m$^2$ 70/30 (w/w) TENCEL/Polyester spunlaced non-woven, was saturated with a 10% (w/w) aqueous solution of glycerol. This saturated non-woven was then dried at 85° C. for approximately 30 minutes. The coating weight of glycerol on the non-woven was approximately 80 g/m$^2$. After drying, the treated non-woven was laminated by hand to the adhesive side of the laminate. The samples were tested a minimum of three days after the lamination step. The average upright MVTR and inverted MVTR values of five test specimens were 1300+/−40 g/m$^2$/24 hours and 3630+/−760 g/m$^2$/24 hours, respectively.

Example 8

The samples were prepared in a similar manner to Example 7, except that the non-woven was saturated with an aqueous solution comprised of 10% (w/w) glycerol and 2.4% (w/w) sodium carbonate monohydrate prior to drying it in the oven. The coating weight of the combined MVTR-modifying materials on the non-woven was 60 g/m$^2$. The average upright MVTR and inverted MVTR values of five test specimens were 2440+/−140 g/m$^2$/24 hours and 19000+/−900 g/m$^2$/24 hours, respectively.

Example 9 (Comparative)

The samples were prepared in a similar manner to Example 7, except that the non-woven was saturated with a 2.6% (w/w) aqueous solution of sodium carbonate monohydrate prior to drying it in the oven. The coating weight of the sodium carbonate monohydrate on the non-woven was 8 g/m$^2$. The average upright MVTR and inverted MVTR values of five test specimens were 1660+/−60 g/m$^2$/24 hours and 18800+/−860 g/m$^2$/24 hours, respectively.

Example 10 (Comparative)

The samples were prepared in a similar manner to Example 7, except that the non-woven, a 40 g/m$^2$ 70/30 (w/w) TENCEL/Polyester spunlaced non-woven, was directly laminated by hand to the adhesive side of the laminate without coating the non-woven with a MVTR-modifying material. The average upright MVTR and inverted MVTR values of up to five test specimens were 1150+/−30 g/m$^2$/24 hours and 2250+/−250 g/m$^2$/24 hours, respectively.

Example 11 (Comparative)

The samples were prepared by first laminating the adhesive from Example 7 to a 25 micron ESTANE 58237 film on paper carrier using a XRL 120 roll laminator (Western Magnum; El Segundo, Calif.) set at approximately 20 psig. A second layer of the adhesive was then laminated using the roll laminator to the first adhesive layer in order to double the thickness of the adhesive. A piece of uncoated non-woven used in Example 1 was then laminated by hand to the adhesive and the paper carrier was removed from the film side of the sample six days prior to testing. The average upright MVTR and inverted MVTR values of four test specimens were 690+/−40 g/m$^2$/24 hours and 1170+/−210 g/m$^2$/24 hours, respectively.

Example 12 (Comparative)

The samples were prepared similar to Example 11 except that the non-woven was coated with sodium carbonate monohydrate at a dried coating weight of 11 g/m$^2$. The average upright MVTR and inverted MVTR values of four test specimens were 1235+/−40 g/m$^2$/24 hours and 20700+/−500 g/m$^2$/24 hours, respectively.

Example 13 (Comparative)

The adhesive on liner in Example 7 was treated with droplets of sterile water via spraying with a spray bottle such that approximately 40% of the adhesive was covered with droplets and then the sample dried in a laboratory oven at 75° C. for 35 minutes. An approximately 25 micron thick polyurethane ESTANE 58237 film on a paper carrier was then laminated to the water treated side of the adhesive on liner using the XRL 120 laminator. Samples were tested six days after the lamination step. The average upright MVTR and inverted MVTR values of five test specimens were 940+/−30 g/m$^2$/24 hours and 1600+/−490 g/m$^2$/24 hours, respectively. The average adhesion to steel of 2.54 cm wide samples was measured to be 294+/−9 g/cm.

Example 14 (Comparative)

This sample was prepared in a similar manner to Example 13 except the adhesive on liner was treated with droplets of an aqueous solution of 1.5% (w/w) sodium carbonate monohydrate via a syringe prior to the drying step. Each droplet weighed approximately 80 mg. The average upright MVTR and inverted MVTR values of five test specimens were 1530+/−40 g/m$^2$/24 hours and 9460+/−950 g/m$^2$/24 hours, respectively. The average adhesion to steel of 2.54 cm wide samples was measured to be 166+/−16 g/cm.

Example 15

This sample was prepared in a similar manner to Example 14 except the adhesive on liner was treated with droplets of an aqueous solution comprised of 4.6% (w/w) sodium carbonate monohydrate, 7.4% glycerol, and 7.4% ethanol (AAPER Alcohol and Chemcial Co., Shelbyville, Ky.) via a syringe prior to the drying step. Each droplet weighed approximately 20 mg. The average upright MVTR and inverted MVTR values of five test specimens were 1880+/−140 g/m$^2$/24 hours and 20900+/−3400 g/m$^2$/24 hours, respectively. The average adhesion to steel of 2.54 cm wide samples was measured to be 170+/−9 g/cm.

Example 16 (Comparative)

For this example, an approximately 28 micron thick layer adhesive of 90/10 (w/w) IOA/AA on polyester liner as described in U.S. Pat. No. 4,737,410 Example 11. An approximately 25 micron thick polyurethane ESTANE 58237 film on a paper carrier was then laminated to the adhesive on liner using the XRL 120 laminator to form the adhesive/film laminate on liner. The non-woven from Example 1, a 40 g/m$^2$ 70/30 (w/w) TENCEL/Polyester spunlaced non-woven, was directly laminated by hand to the adhesive side of the laminate without MVTR-modifying material and the paper carrier was removed from the film side of the sample. Four specimens were tested six days after construction of the samples. The average upright MVTR and inverted MVTR values were 640+/−15 g/m$^2$/24 hours and 1090+/−30 g/m$^2$/24 hours, respectively.

Example 17

The samples were prepared in a similar manner to Example 16, with a 28 micron thick layer adhesive, except that the non-woven was saturated with an aqueous solution of a mixture of 2.5% (w/w) of sodium carbonate monohydrate and 5% (w/w) glycerol and then dried at 75° C. for approximately 30 minutes. The combined coating weight of the sodium carbonate monohydrate and glycerol on the non-woven was 50 g/m$^2$. MVTR testing was conducted five days after lamination of the treated non-woven to the adhesive side of the adhesive/film laminate. The average upright MVTR and inverted MVTR values of four test specimens were 960+/−60 g/m$^2$/24 hours and 1340+/−120 g/m$^2$/24 hours, respectively.

Example 18 (Comparative)

The samples were prepared in a similar manner to Example 16 except that the adhesive was only 18 microns thick. The average upright MVTR and inverted MVTR values of four test specimens were 820+/−15 g/m$^2$/24 hours and 1180+/−20 g/m$^2$/24 hours, respectively.

Example 19

The samples were prepared in a similar manner to Example 17 except that the adhesive was only 18 microns thick. The average upright MVTR and inverted MVTR values of four or three test specimens were 1310+/−40 g/m$^2$/24 hours and 5460+/−720 g/m$^2$/24 hours, respectively.

Example 20 (Comparative)

The samples were prepared in a similar manner to Example 19 except that the non-woven was saturated with an aqueous solution of 2.5% (w/w) of sodium carbonate monohydrate and the coating weight of sodium carbonate monohydrate on the dried non-woven was 11 g/m$^2$. The average upright MVTR and inverted MVTR values of four test specimens were 900+/−30 g/m$^2$/24 hours and 1440+/−50 g/m$^2$/24 hours, respectively.

Example 21

The samples were prepared in a similar manner to Example 20 including the adhesive layer being approximately 18 microns thick, except that the non-woven was saturated with an aqueous solution of 2% (w/w) of methyldiethanol amine prior to drying. The coating weight of the methyldiethanol amine on the non-woven was 4 g/m$^2$. The average upright MVTR and inverted MVTR values of four test specimens were 1780+/−80 g/m²/24 hours and 1810+/−180 g/m²/24 hours, respectively.

Example 22

The samples were prepared in a similar manner to Example 17, except that the non-woven was saturated with an aqueous solution of 2% (w/w) of methydiethanol amine prior to drying. The coating weight of the methyldiethanol amine on the non-woven was 4 g/m². The adhesive thickness was approximately 28 microns. The average upright MVTR and inverted MVTR values of four test specimens were 1340+/−30 g/m²/24 hours and 1260+/−50 g/m²/24 hours, respectively.

Example 23 (Comparative)

An 18 micron thick pressure sensitive adhesive on polyester liner was made in a manner described in U.S. Pat. No. 4,737,410, but with the following monomers and ratios: 25/69/6 2-EHA/BA/AA (w/w/w). The adhesive was then laminated to the 25 micron thick polyurethane ESTANE 58237 film on paper carrier. The non-woven from Example 1 was then laminated to the adhesive side of the film/adhesive laminate. Four specimens were tested six days after construction of the samples. The average upright MVTR and inverted MVTR values were 1500+/−30 g/m²/24 hours and 2400+/−160 g/m²/24 hours, respectively.

Example 24 (Comparative)

The samples were prepared in a similar manner to Example 23 except that the non-woven was saturated with an aqueous solution of 2.5% (w/w) of sodium carbonate monohydrate and then dried at 85° C. for approximately 30 minutes prior to the lamination to the adhesive. The resulting coating weight of sodium carbonate monohydrate on the non-woven was 11 g/m². The average upright MVTR and inverted MVTR values of four test specimens were 1570+/−80 g/m²/24 hours and 2540+/−60 g/m²/24 hours, respectively.

Example 25

The samples were prepared in a similar manner to Example 23 except that the non-woven was saturated with an aqueous solution of a mixture of 2.5% (w/w) of sodium carbonate monohydrate and 5% (w/w) glycerol and then dried at 75° C. for approximately 30 minutes prior to lamination to the adhesive. The combined coating weight of the sodium carbonate monohydrate and glycerol on the non-woven was 50 g/m². MVTR testing was conducted five days after lamination of the treated non-woven to the adhesive side of the adhesive/film laminate. The average upright MVTR and inverted MVTR values of four test specimens were 2000+/−50 g/m²/24 hours and 3230+/−400 g/m²/24 hours, respectively.

Example 26

The samples were prepared in a similar manner to Example 23 except that the non-woven was saturated with an aqueous solution of a mixture of 2% (w/w) of methydiethanol amine prior to drying at 75° C. for approximately 30 minutes. The coating weight of the methyldiethanol amine on the non-woven was 4 g/m². MVTR testing was conducted five days after lamination of the treated non-woven to the adhesive side of the adhesive/film laminate. The average upright MVTR and inverted MVTR values of four test specimens were 2000+/−40 g/m²/24 hours and 2950+/−320 g/m²/24 hours, respectively.

Example 27 (Comparative)

An approximately 22 micron thick layer of 90/10 (w/w) IOA/AA pressure sensitive adhesive was pressure laminated to an approximately 25 micron thick polyurethane ESTANE 58237 film on a paper carrier. The untreated non-woven from Example 1, a 40 g/m² 70/30 (w/w) TENCEL/Polyester spunlaced non-woven was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 920+/−10 g/m²/24 hours and 1460+/−140 g/m²/24 hours, respectively.

Example 28

The samples were prepared and tested in a similar manner to Example 27 except the non-woven was saturated with a 2% (w/w) solution of methyl diethanolamine, dried at 75° C. for 30 minutes, and then laminated to the adhesive. The average upright MVTR and inverted MVTR values of four test specimens were 1700+/−40 g/m²/24 hours and 1840+/−180 g/m²/24 hours, respectively.

Example 29 (Comparative)

The samples were prepared and tested in a similar manner to Example 27 except the non-woven was saturated with a 5% (w/w) solution of glycerol prior to drying at 75° C. for 30 minutes and lamination to the adhesive. The coating weight of glycerol on the non-woven was approximately 10 g/m². The average upright MVTR and inverted MVTR values of four test specimens were 970+/−10 g/m²/24 hours and 1490+/−30 g/m²/24 hours, respectively.

Example 30

The samples were prepared and tested in a similar manner to Example 27 except the non-woven was saturated with an aqueous solution containing 5% (w/w) of glycerol and 3% (w/w) of sodium carbonate monohydrate prior to drying at 75° C. for 30 minutes and lamination to the adhesive. The combined coating weight of the sodium carbonate monohydrate and the glycerol on the non-woven was approximately 28 g/m². The average upright MVTR and inverted MVTR values of four test specimens were 1140+/−40 g/m²/24 hours and 1710+/−230 g/m²/24 hours, respectively.

Example 31 (Comparative)

The samples were prepared and tested in a similar manner to Example 27 except the non-woven was saturated with a 3% (w/w) aqueous solution of sodium carbonate monohydrate prior to drying at 75° C. for 30 minutes and lamination to the adhesive. The coating weight of the dried sodium carbonate monohydrate on the non-woven was approximately 11 g/m². The average upright MVTR and inverted MVTR values of four test specimens were 1040+/−60 g/m²/24 hours and 1570+/−100 g/m²/24 hours, respectively.

Example 32 (Comparative)

A 22 micron thick pressure sensitive adhesive was made in a manner described in U.S. Pat. No. 4,737,410, but with the following monomers and ratios: 46.5/46/7.5 2-EHA/BA/AA (w/w/w). The pressure sensitive adhesive was pressure laminated to an approximately 25 micron thick polyurethane ESTANE 58237 film on a paper carrier. The untreated non-woven from Example 1, a 40 g/m$^2$ 70/30 (w/w) TENCEL/Polyester spunlaced non-woven, was then laminated by hand to the adhesive side of the adhesive/film laminate and the paper carrier was removed from the film side of the sample. Samples were tested seven days after lamination of the non-woven to the adhesive. The average upright MVTR and inverted MVTR values of four test specimens were 1560+/−30 g/m$^2$/24 hours and 2470+/−110 g/m$^2$/24 hours, respectively.

Example 33

The samples were prepared and tested in a similar manner to Example 32 except the non-woven was saturated with a 2% (w/w) solution of methyl diethanolamine, dried at 75° C. for 30 minutes, and then laminated to the adhesive. The average upright MVTR and inverted MVTR values of four test specimens were 1970+/−70 g/m$^2$/24 hours and 3010+/−220 g/m$^2$/24 hours, respectively.

Example 34 (Comparative)

The samples were prepared and tested in a similar manner to Example 33 except the non-woven was saturated with a 5% (w/w) solution of (instead of the methyl diethanolamine solution) prior to the drying step. The coating weight of glycerol on the non-woven was approximately 10 g/m$^2$. The average upright MVTR and inverted MVTR values of four test specimens were 1640+/−20 g/m$^2$/24 hours and 2600+/−90 g/m$^2$/24 hours, respectively.

Example 35

The samples were prepared and tested in a similar manner to Example 33 except the non-woven was saturated with an aqueous solution containing 5% (w/w) of glycerol and 3% (w/w) of sodium carbonate monohydrate (instead of the methyl diethanolamine solution) prior to the drying step. The combined coating weight of the sodium carbonate monohydrate and the glycerol on the non-woven was approximately 28 g/m$^2$. The average upright MVTR and inverted MVTR values of four test specimens were 1670+/−10 g/m$^2$/24 hours and 2740+/−60 g/m$^2$/24 hours, respectively.

Example 36 (Comparative)

The samples were prepared and tested in a similar manner to Example 33 except the non-woven was saturated with a 3% (w/w) aqueous solution of sodium carbonate monohydrate (instead of the methyl diethanolamine solution) prior to the drying step. The coating weight of the sodium carbonate monohydrate on the non-woven was approximately 11 g/m$^2$. The average upright MVTR and inverted MVTR values of four test specimens were 1590+/−10 g/m$^2$/24 hours and 2590+/−130 g/m$^2$/24 hours, respectively.

Example 37 (Comparative)

For this example, an approximately 25 micron thick layer of adhesive on paper liner as described in U.S. Pat. No. 4,737,410 Example 31 with less than 1% polyethyloxazoline was used. The adhesive on liner was pressure laminated to an approximately 25 micron thick polyurethane ESTANE 58237 film on a paper carrier. Droplets of sterile water were applied to the adhesive side of this adhesive/film laminate using a syringe such that the droplets covered approximately 50% of the adhesive surface. The weight of a droplet was approximately 14 mg. The coated sample was then placed in an oven at 80° C. for 30 minutes. The treated adhesive/film laminate samples were tested approximately seven days after the lamination step. The average upright MVTR and inverted MVTR values of five test specimens were 1090+/−50 g/m$^2$/24 hours and 1550+/−70 g/m$^2$/24 hours, respectively. The average adhesion to steel of 2.54 cm wide samples was measured to be 205+/−14 g/cm.

Example 38 (Comparative)

The samples were prepared similar to Example 37 except that after application of the droplets of water to the adhesive side of the laminate, the water was spread across the adhesive layer by passing a spoon across the water droplets. The coated sample was then placed in an oven at 80° C. for 30 minutes. The treated adhesive/film laminate samples were tested approximately seven days after the lamination step. The average upright MVTR and inverted MVTR values of five test specimens were 1110+/−50 g/m$^2$/24 hours and 1580+/−80 g/m$^2$/24 hours, respectively. The average adhesion to steel of 2.54 cm wide samples was measured to be 180+/−20 g/cm.

Example 39

The samples were prepared similar to Example 37 except that droplets of an aqueous mixture of 2% (w/w) sodium carbonate monohydrate and 1.8% (w/w) glycerine were applied to the adhesive side of the adhesive/film laminate prior to the drying step. The average upright MVTR and inverted MVTR values of five test specimens were 1700+/−90 g/m$^2$/24 hours and 7900+/−1000 g/m$^2$/24 hours, respectively. The average adhesion to steel of 2.54 cm wide samples was measured to be 170+/−10 g/cm.

Example 40

The samples were prepared similar to Example 38 except that droplets of an aqueous mixture of 2% (w/w) sodium carbonate monohydrate and 1.8% (w/w) glycerine were applied to the adhesive side of the adhesive/film laminate before spreading the droplets on the adhesive with a spoon. The average upright MVTR and inverted MVTR values of five test specimens were 2600+/−250 g/m$^2$/24 hours and 27300+/−3400 g/m$^2$/24 hours, respectively. The average adhesion to steel of 2.54 cm wide samples was measured to be 120+/−14 g/cm.

Example 41 (Comparative)

The samples were prepared similar to Example 37 except that before the addition of the water droplets, two layers of adhesive were laminated to the urethane film which resulted in an adhesive/film laminate whose adhesive thickness was approximately 50 microns. The average upright MVTR and inverted MVTR values of five test specimens were 700+/−40 g/m$^2$/24 hours and 970+/−70 g/m$^2$/24 hours, respectively.

The average adhesion to steel of 2.54 cm wide samples was measured to be 230+/−15 g/cm.

Example 42 (Comparative)

The samples were prepared similar to Example 38 except that before addition of the water droplets and spreading of the water layer, two layers of adhesive were laminated to the urethane film which resulted in an adhesive/film laminate whose adhesive thickness was approximately 50 microns. The average upright MVTR and inverted MVTR values of five test specimens were 690+/−30 g/m$^2$/24 hours and 900+/−10 g/m$^2$/24 hours, respectively. The average adhesion to steel of 2.54 cm wide samples was measured to be 230+/−20 g/cm.

Example 43

The samples were prepared similar to Example 41, except that the MVTR-modifying material droplets were an aqueous solution of 2% (w/w) sodium carbonate monohydrate and 1.8% (w/w) glycerine. The average upright MVTR and inverted MVTR values of five test specimens were 1390+/−50 g/m$^2$/24 hours and 7440+/−680 g/m$^2$/24 hours, respectively. The average adhesion to steel of 2.54 cm wide samples was measured to be 220+/−10 g/cm.

Example 44

The samples were prepared similar to Example 42, except that the MVTR-modifying material droplets (before spreading on the adhesive) were an aqueous solution of 2% (w/w) sodium carbonate monohydrate and 1.8% (w/w) glycerine. The average upright MVTR and inverted MVTR values of five test specimens were 1340+/−60 g/m$^2$/24 hours and 10000+/−1200 g/m$^2$/24 hours, respectively. The average adhesion to steel of 2.54 cm wide samples was measured to be 170+/−20 g/cm.

TABLE 2

Summary of Experimental results for Examples 1-44

| Example | Adhesive | Backing | MVTR Modifying Composition | Upright (Dry) MVTR g/m$^2$/24 hr +/− Std Dev | Inverted (Wet) MVTR g/m$^2$/24 hr +/− Std Dev |
|---|---|---|---|---|---|
| 1 Comp. | 65/15/20 2-EHA/AA/ Pluronic 25R4 | PU film (58237 resin) | None | 1150 +/− 100 | 2340 +/− 190 |
| 2 Comp. | 65/15/20 2-EHA/AA/ Pluronic 25R4 | PU film (58237 resin) | Na-citrate | 1000 +/− 30 | 2350 +/− 90 |
| 3 Comp. | 65/15/20 2-EHA/AA/ Pluronic 25R4 | PU film (58237 resin) | Citric acid | 1180 +/− 60 | 1720 +/− 40 |
| 4 Comp. | 65/15/20 2-EHA/AA/ Pluronic 25R4 | PU film (58237 resin) | Na-carbonate monohydrate | 1070 +/− 40 | 20800 +/− 980 |
| 5 | 65/15/20 2-EHA/AA/ Pluronic 25R4 | PU film (58237 resin) | Methyl diethanolamine | 2160 +/− 80 | 19800 +/− 940 |
| 6 Comp. | 65/15/20 2-EHA/AA/ Pluronic 25R4 | PU film (58237 resin) | Polyethylene glycol 400 | 1530 +/− 50 | 2290 +/− 90 |
| 7 Comp. | 70/15/15 (IOA/AA/EOA + less than 1% PEOX) | PU film (58237 resin) | Glycerol | 1300 +/− 40 | 3630 +/− 760 |
| 8 | 70/15/15 (IOA/AA/EOA + less than 1% PEOX) | PU film (58237 resin) | Glycerol + Na-carbonate monohydrate | 2440 +/− 140 | 19000 +/− 900 |
| 9 Comp. | 70/15/15 (IOA/AA/EOA + less than 1% PEOX) | PU film (58237 resin) | Na-carbonate monohydrate | 1660 +/− 60 | 18800 +/− 860 |
| 10 Comp. | 70/15/15 (IOA/AA/EOA + less than 1% PEOX) | PU film (58237 resin) | None | 1150 +/− 30 | 2520 +/− 250 |
| 11 Comp. | 2X thickness of 70/15/15 (IOA/AA/EOA + less than 1% PEOX) | PU film (58237 resin) | None | 690 +/− 40 | 1170 +/− 210 |
| 12 Comp. | 2X thickness of 70/15/15 (IOA/AA/EOA + less than 1% PEOX) | PU film (58237 resin) | Na-carbonate monohydrate | 1235 +/− 100 | 20700 +/− 500 |
| 13 Comp. | 70/15/15 (IOA/AA/EOA + less than 1% PEOX) | PU film (58237 resin) | none | 940 +/− 30 | 1600 +/− 490 |

TABLE 2-continued

Summary of Experimental results for Examples 1-44

| Example | Adhesive | Backing | MVTR Modifying Composition | Upright (Dry) MVTR $g/m^2/24$ hr +/− Std Dev | Inverted (Wet) MVTR $g/m^2/24$ hr +/− Std Dev |
|---|---|---|---|---|---|
| 14 Comp. | 70/15/15 (IOA/AA/EOA + less than 1% PEOX) | PU film (58237 resin) | Droplets of Na-carbonate monohydrate | 1530 +/− 30 | 9460 +/− 490 |
| 15 | 70/15/15 (IOA/AA/EOA + less than 1% PEOX) | PU film (58237 resin) | Droplets of Na-carbonate monohydrate + glycerol | 1880 +/− 140 | 20900 +/− 3400 |
| 16 Comp. | 90/10 (IOA/AA) | PU film (58237 resin) | none | 640 +/− 15 | 1090 +/− 30 |
| 17 | 90/10 (IOA/AA) | PU film (58237 resin) | Na-carbonate monohydrate + glycerol | 960 +/− 60 | 1340 +/− 120 |
| 18 Comp. | 90/10 (IOA/AA) | PU film (58237 resin) | none | 820 +/− 15 | 1180 +/− 20 |
| 19 | 90/10 (IOA/AA) | PU film (58237 resin) | Na-carbonate monohydrate + glycerol | 1310 +/− 40 | 5460 +/− 720 |
| 20 Comp. | 90/10 (IOA/AA) | PU film (58237 resin) | Na-carbonate monohydrate | 900 +/− 30 | 1440 +/− 50 |
| 21 | 90/10 (IOA/AA) 18 microns thick | PU film (58237 resin) | Methyl diethanolamine | 1780 +/− 80 | 1810 +/− 180 |
| 22 | 90/10 (IOA/AA) 28 microns thick | PU film (58237 resin) | Methyl diethanolamine | 1330 +/− 40 | 1260 +/− 50 |
| 23 Comp. | 25/69/6 (2-EHA/BA/AA) | PU film (58237 resin) | none | 1500 +/− 30 | 2400 +/− 160 |
| 24 Comp. | 25/69/6 (2-EHA/BA/AA) | PU film (58237 resin) | Na-carbonate monohydrate | 1570 +/− 80 | 2540 +/− 60 |
| 25 | 25/69/6 (2-EHA/BA/AA) | PU film (58237 resin) | Na-carbonate monohydrate + glycerol | 2000 +/− 50 | 3230 +/− 400 |
| 26 | 25/69/6 (2-EHA/BA/AA) | PU film (58237 resin) | Methyl diethanolamine | 2000 +/− 40 | 2950 +/− 320 |
| 27 Comp. | 90/10 (IOA/AA) | PU film (58237 resin) | none | 920 +/− 10 | 1460 +/− 140 |
| 28 | 90/10 (IOA/AA) | PU film (58237 resin) | Methyl diethanolamine | 1700 +/− 40 | 1840 +/− 180 |
| 29 Comp. | 90/10 (IOA/AA) | PU film (58237 resin) | glycerol | 970 +/− 10 | 1490 +/− 30 |
| 30 | 90/10 (IOA/AA) | PU film (58237 resin) | Glycerol + Na carbonate monohydrate | 1140 +/− 40 | 1710 +/− 230 |
| 31 Comp. | 90/10 (IOA/AA) | PU film (58237 resin) | Na-carbonate monohydrate | 1040 +/− 60 | 1570 +/− 100 |
| 32 Comp. | 46.5/46/7.5 2-EHA/BA/AA | PU film (58237 resin) | none | 1560 +/− 30 | 2470 +/− 110 |
| 33 | 46.5/46/7.5 2-EHA/BA/AA | PU film (58237 resin) | Methyl diethanolamine | 1970 +/− 70 | 3010 +/− 220 |
| 34 | 46.5/46/7.5 2-EHA/BA/AA | PU film (58237 resin) | glycerol | 1640 +/− 20 | 2600 +/− 90 |
| 35 | 46.5/46/7.5 2-EHA/BA/AA | PU film (58237 resin) | Glycerol + Na-carbonate monohydrate | 1670 +/− 20 | 2740 +/− 60 |
| 36 Comp. | 46.5/46/7.5 2-EHA/BA/AA | PU film (58237 resin) | Na-carbonate monohydrate | 1590 +/− 10 | 2590 +/− 130 |

TABLE 2-continued

Summary of Experimental results for Examples 1-44

| Example | Adhesive | Backing | MVTR Modifying Composition | Upright (Dry) MVTR g/m²/24 hr +/− Std Dev | Inverted (Wet) MVTR g/m²/24 hr +/− Std Dev |
|---|---|---|---|---|---|
| 37 Comp. | 70/15/15 (IOA/AA/EOA + less than 1% PEOX) | PU film (58237 resin) | Water droplets | 1090 +/− 50 | 1550 +/− 70 |
| 38 Comp. | 70/15/15 (IOA/AA/EOA + less than 1% PEOX) | PU film (58237 resin) | Water droplets then spread | 1110 +/− 50 | 1580 +/− 80 |
| 39 | 70/15/15 (IOA/AA/EOA + less than 1% PEOX) | PU film (58237 resin) | Droplets of glycerol + Na-carbonate monohydrate | 1700 +/− 90 | 7900 +/− 1000 |
| 40 | 70/15/15 (IOA/AA/EOA + less than 1% PEOX) | PU film (58237 resin) | Droplets of glycerol + Na-carbonate monohydrate then spread | 2600 +/− 250 | 27300 +/− 3400 |
| 41 Comp. | 50 micron thick 70/15/15 (IOA/AA/EOA + less than 1% PEOX) | PU film (58237 resin) | Water droplets | 700 +/− 40 | 970 +/− 70 |
| 42 Comp. | 50 micron thick 70/15/15 (IOA/AA/EOA + less than 1% PEOX) | PU film (58237 resin) | Water droplets then spread | 690 +/− 30 | 900 +/− 10 |
| 43 | 50 micron thick 70/15/15 (IOA/AA/EOA + less than 1% PEOX) | PU film (58237 resin) | Droplets of glycerol + Na-carbonate monohydrate | 1390 +/− 50 | 7440 +/− 680 |
| 44 | 50 micron thick 70/15/15 (IOA/AA/EOA + less than 1% PEOX) | PU film (58237 resin) | Droplets of glycerol + Na-carbonate monohydrate then spread | 1340 +/− 60 | 10000 +/− 1200 |

2-EHA = 2-ethylhexylacrylate
AA = Acrylic Acid
BA = butyl acrylate
EOA = methoxy poly(ethylene oxide) acrylate macromer
IOA = iso-octylacrylate
Na = sodium
PEOX = poly(ethyloxazoline)
Pluronic 25R4 = poly(ethylene polypropylene) copolymer diol from BASF, Mount Olive, NJ
PU = polyurethane

EMBODIMENTS

1. A method of increasing the moisture vapor transmission rate of an adhesive layer in a medical article, the method comprising: providing a PSA layer comprising acid-functional groups or basic-functional groups, wherein the PSA includes at least 0.84 mmoles acidic- or basic-functional groups per gram PSA; providing an MVTR-modifying composition comprising an MVTR-modifying material that is basic when the PSA comprises an acidic-functional group or is acidic when the PSA comprises a basic-functional group, wherein the MVTR-modifying composition is miscible with the PSA; and placing the MVTR-modifying composition in contact with the PSA under conditions effective for at least a portion of the MVTR-modifying composition to penetrate into the PSA layer; wherein contact between the MVTR-modifying material and the PSA causes an acid-base reaction to form a poly-salt and increase the moisture permeability of at least a portion of the PSA layer.

2. A method of increasing the moisture vapor transmission rate of an adhesive layer in a medical article, the method comprising: providing a PSA layer comprising acid-functional groups or basic-functional groups; providing an MVTR-modifying composition comprising an MVTR-modifying material that is basic when the PSA comprises an acidic-functional group or is acidic when the PSA comprises a basic-functional group, wherein the MVTR-modifying composition is miscible with the PSA; and placing the MVTR-modifying composition in contact with the PSA under conditions effective for at least a portion of the MVTR-modifying composition to penetrate into the PSA layer to form a non-uniform dispersion; wherein contact between the MVTR-modifying material and the PSA causes an acid-base reaction to form a poly-salt and increase the moisture permeability of at least a portion of the PSA layer.

3. The method of embodiment 1 or embodiment 2 wherein the MVTR-modifying composition further comprises a plasticizer.

4. The method of embodiment 3 wherein the plasticizer comprises glycerine, propylene glycol, sorbitol, xylitol, maltitol, polydextrose, glyceryl triacetate, lactic acid, urea, hydroxyethylurea, glucose, poly(vinyl alcohol), polyethylene glycols, liquid amines such as triethanolamine, diethanolamine, monoethanolamine, methyldiethanolamine, block copolymers of polyethylene glycol or propylene glycol, and combinations thereof 5. The method of embodiment 3 or embodiment 4 wherein the MVTR-modifying composition comprises an inorganic acid or an inorganic base.

6. The method of any one of embodiments 1 through 4 wherein the MVTR-modifying composition comprises an organic acid or an organic base.

7. The method of any one of embodiments 1 through 6 wherein placing the MVTR-modifying composition in contact with the PSA comprises pattern coating the MVTR-modifying composition on the PSA layer.

8. The method of any one of embodiments 1 through 6 wherein placing the MVTR-modifying composition in contact with the PSA comprises: providing a scaffold; coating the scaffold with the MVTR-modifying composition; and contacting at least a portion of the PSA layer with the coated scaffold.

9. The method of any one of embodiments 1 through 8 wherein the PSA layer comprises a (meth)acrylate polymer, and wherein said polymer is prepared from at least 6 wt-% acidic- or basic-functional monomers, based on the total weight of the PSA.

10. The method of any one of embodiments 1 through 9 wherein the PSA includes no greater than 4.2 mmoles acidic- or basic-functional groups per gram PSA.

11. The method of any one of embodiments 1 through 10 further comprising providing a backing, and placing the PSA in contact with the backing before or after placing the MVTR-modifying composition in contact with the PSA layer.

12. The method of any one of embodiments 1 through 11 further comprising providing a pH-altering layer, and applying the pH-altering layer on the PSA layer after placing the MVTR-modifying composition in contact with the PSA layer.

13. The method of embodiments 12 wherein the pH-altering layer comprises a pH-altering material selected from a group consisting of citric acid, polyacrylic acid, or combinations thereof.

14. The method of any one of embodiments 1 through 13 further comprising providing a filtration layer, and applying the filtration layer on the PSA layer after placing the MVTR-modifying composition in contact with the PSA layer.

15. The method of any one of embodiments 1 through 11 wherein the molar ratio of the MVTR-modifying material to the functional groups is 0.1:1 to 100:1.

16. The method of any one of embodiments 1 through 15 wherein the PSA layer comprises a polymer having acid-functional groups, and the MVTR-modifying composition is basic.

17. The method of embodiment 16 wherein the MVTR-modifying composition comprises a base selected from a group consisting of sodium hydroxide, potassium hydroxide, calcium hydroxide, lithium hydroxide, silver hydroxide, zinc hydroxide, ammonium hydroxide, magnesium hydroxide, barium hydroxide, strontium hydroxide, cesium hydroxide, rubidium hydroxide, ammonium carbonate, sodium carbonate, sodium bicarbonate, potassium carbonate, potassium bicarbonate, silver carbonate, lithium carbonate, lithium bicarbonate, barium bicarbonate, magnesium carbonate, cesium carbonate, triethanolamine, methyldiethanolamine, pyridine, benzimidizole, histidine, triethylamine, monoethanolamine, diethanolamine, hydrates thereof, and combinations thereof.

18. The method of any one of embodiments 1 through 15 wherein the PSA layer comprises a polymer having basic functional groups, and the MVTR-modifying composition is acidic.

19. The method of embodiment 18 wherein the MVTR-modifying composition comprises an acid selected from a group consisting of formic acid, acetic acid, lactic acid, sulfuric acid, hydrochloric acid, nitric acid, phosphoric acid, or combinations thereof.

20. The method of any one of embodiments 1 through 19 wherein the PSA comprises rubber based adhesives, (meth)acrylics, poly(alpha-olefin)s, polyurethane, silicones, and combinations thereof.

21. The method of any one of embodiments 1 through 20 wherein the medical article has a wet MVTR of at least 1200 $g/m^2/24$ hours.

22. The method of any one of embodiments 1 through 21 wherein the MVTR-modifying composition improves the wet MVTR of the medical article by at least 20% relative to the same medical article without the MVTR-modifying composition.

23. The method of any one of embodiments 1 through 22 wherein the MVTR-modifying composition improves the dry MVTR of the medical article by at least 20% relative to the same medical article without the MVTR-modifying composition.

24. A method of applying a plasticizer to a PSA layer in a medical article, the method comprising: providing a PSA layer comprising acid-functional groups or basic-functional groups; providing a plasticizer; providing a scaffold; coating the scaffold with the plasticizer; and contacting at least a portion of the PSA layer with the coated scaffold.

25. A medical article prepared by the method of any one of embodiments 1 through 24.

26. The medical article of embodiment 25 which is a wound dressing.

27. A medical article comprising:
    a PSA layer comprising a PSA comprising acid-functional groups or basic-functional groups; an MVTR-modifying composition that is basic when the PSA comprises an acidic-functional group or is acidic when the PSA comprises a basic-functional group; and ionic groups non-uniformly distributed throughout the PSA layer, wherein the ionic groups are formed from the reaction of the PSA functional groups and the MVTR-modifying composition.

28. The medical article of embodiment 27, wherein the MVTR-composition further comprises a plasticizer.

29. The medical article of embodiment 27, wherein the PSA includes at least 0.84 mmoles acidic- or basic-functional groups per gram PSA.

30. A medical article comprising:
    a PSA layer comprising acid-functional groups or basic-functional groups, wherein the PSA includes at least 0.84 mmoles acidic- or basic-functional groups per gram PSA; a hydrophilic plasticizer; and an MVTR-modifying material that is basic when the PSA comprises acidic-functional groups or is acidic when the PSA comprises basic-functional groups; wherein the MVTR-modifying material is immiscible with the PSA, and reacts with the functional groups of the PSA upon contact to form a poly-salt in the presence of fluid.

31. A wound dressing comprising:
a backing having a first major surface and a second major surface; a PSA layer disposed on at least a portion of the first major surface of the backing; wherein the PSA comprises acid-functional groups or basic-functional groups, wherein the PSA includes at least 0.84 mmoles acidic- or basic-functional groups per gram PSA; a hydrophilic plasticizer; and an MVTR-modifying layer proximate the PSA layer; wherein the MVTR-modifying layer comprises an MVTR-modifying material that is basic when the PSA comprises acidic-functional groups, or is acidic when the PSA comprises basic-functional groups; wherein the MVTR-modifying material is immiscible with the PSA, and reacts with the functional groups to form a poly-salt upon contact in the presence of fluid.

32. A wound dressing comprising:
a backing having a first major surface and a second major surface; a PSA layer disposed on at least a portion of the first major surface of the backing; wherein the PSA layer comprises acid-functional groups; a support layer releasably adhered to the second major surface of the backing; a hydrophilic plasticizer; and an MVTR-modifying layer comprising an MVTR-modifying material in contact with the PSA layer, wherein the PSA layer does not include MVTR-modifying material uniformly dispersed throughout; wherein the MVTR-modifying material is basic, is immiscible with the PSA, and reacts with the functional groups to form a poly-salt upon contact in the presence of fluid.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of increasing moisture vapor transmission of an adhesive layer in a medical article, the method comprising:
providing a PSA composition comprising a combination of hydrophilic polymer components and acid functional groups, the combination being greater than 15 wt %; wherein the hydrophilic polymer components are greater than 3 wt % and less than 30 wt %; wherein the acid functional groups are greater than 6 wt %, wherein all weight percentages are based on total weight of the PSA composition;
forming a PSA layer from the PSA composition;
providing an MVTR-modifying composition comprising an organic base, wherein the MVTR-modifying composition is not mixed within the PSA composition, but is miscible with the PSA composition;
forming an MVTR-modifying layer from the MVTR-modifying composition; and
placing the MVTR-modifying layer proximate the PSA layer under conditions effective for at least a portion of the MVTR-modifying composition to penetrate into the PSA composition to form a non-uniform dispersion throughout the PSA layer; wherein contact between the MVTR-modifying composition and the PSA composition causes an acid-base reaction to form a poly-salt and increase moisture permeability of at least a portion of the PSA layer.

2. The method of claim 1 wherein the MVTR-modifying composition further comprises a plasticizer.

3. The method of claim 2 wherein the plasticizer comprises glycerine, propylene glycol, sorbitol, xylitol, maltitol, polydextrose, glyceryl triacetate, lactic acid, urea, hydroxyethylurea, glucose, poly(vinyl alcohol), polyethylene glycols, liquid amines such as triethanolamine, diethanolamine, monoethanolamine, methyldiethanolamine, block copolymers of polyethylene glycol or propylene glycol, and combinations thereof.

4. The method of claim 1 wherein the PSA composition includes at least 0.84 mmoles acidic-functional groups per gram PSA composition.

5. The method of claim 1 wherein the PSA composition comprises a (meth)acrylate polymer, and wherein said polymer is prepared from at least 6 wt-% acidic- or basic-functional monomers, based on total weight of the PSA composition.

6. The method of claim 1 further comprising providing a backing, and forming a PSA layer on the backing before or after placing the MVTR-modifying layer proximate the PSA layer.

7. The method of claim 1 further comprising providing a pH-altering layer, and applying the pH-altering layer on the PSA layer after placing the MVTR-modifying layer proximate the PSA layer, wherein the pH-altering layer comprises a pH-altering material selected from a group consisting of citric acid, polyacrylic acid, and combinations thereof.

8. The method of claim 1 further comprising providing a filtration layer, and applying the filtration layer on the PSA layer after placing the MVTR-modifying layer proximate the PSA layer.

9. The method of claim 1 wherein the MVTR-modifying layer comprises an organic base selected from a group consisting of triethanolamine, methyldiethanolamine, pyridine, benzimidizole, histidine, triethylamine, monoethanolamine, diethanolamine, hydrates thereof, and combinations thereof.

10. The method of claim 1 wherein the medical article has a wet MVTR of at least 1200 g/m$^2$/24 hours.

11. The method of claim 1 wherein the medical article is a wound dressing.

12. A method of increasing moisture vapor transmission of an adhesive layer in a medical article, the method comprising:
providing a PSA composition comprising a combination of hydrophilic polymer components and acid functional groups, the combination being greater than 15 wt %; wherein the hydrophilic polymer components are greater than 3 wt % and less than 30 wt %; wherein the acid functional groups are greater than 6 wt %, wherein all weight percentages are based on total weight of the PSA composition;
forming a PSA layer from the PSA composition;
providing an MVTR-modifying composition comprising an organic base, wherein the MVTR-modifying composition is not mixed within the PSA composition, but is miscible with the PSA composition;
forming an MVTR-modifying layer from the MVTR-modifying composition; wherein forming an MVTR-modifying layer comprises:

providing a scaffold; and
coating the scaffold with the MVTR-modifying composition to form the MVTR-modifying layer; and
placing the MVTR-modifying layer proximate the PSA layer.

13. A wound dressing prepared by the method of claim 1.

* * * * *

UNITED STATES PATENT AND TRADEMARK OFFICE
CERTIFICATE OF CORRECTION

PATENT NO. : 10,500,302 B2
APPLICATION NO. : 12/942434
DATED : December 10, 2019
INVENTOR(S) : David Holm Page 1 of 1

It is certified that error appears in the above-identified patent and that said Letters Patent is hereby corrected as shown below:

In the Specification

<u>Column 3</u>
Line 4          Delete "polypropylene" and insert -- poly(propylene --, therefor.

<u>Column 12</u>
Line 4          Delete "backing)" and insert -- backing). --, therefor.

<u>Column 15</u>
Line 65         Delete "backing" and insert -- backing. --, therefor.

<u>Column 19</u>
Line 39         Delete "backings" and insert -- backings. --, therefor.

<u>Column 26</u>
Line 61         Delete "polypropylene" and insert -- poly(propylene --, therefor.

Signed and Sealed this
Ninth Day of June, 2020

Andrei Iancu
*Director of the United States Patent and Trademark Office*